(12) United States Patent
Anderson et al.

(10) Patent No.: US 11,170,213 B2
(45) Date of Patent: Nov. 9, 2021

(54) OCULAR IMAGE CAPTURING DEVICE

(71) Applicants: OPTOS PLC, Dunfermline (GB);
NIKON CORPORATION, Tokyo (JP)

(72) Inventors: Alan Anderson, Scotland (GB);
Praveen Ashok, Scotland (GB);
Tomoharu Fujiwara, Tokyo (JP);
Yasushi Tanabe, Tokyo (JP); Hiroshi Kintou, Tokyo (JP); Mariko Hirokawa, Tokyo (JP); Tadashi Umezaki, Tokyo (JP)

(73) Assignee: OPTOS PLC, Dunfermline (GB)

( * ) Notice: Subject to any disclaimer, the term of this patent is extended or adjusted under 35 U.S.C. 154(b) by 88 days.

(21) Appl. No.: 16/335,169

(22) PCT Filed: Oct. 10, 2017

(86) PCT No.: PCT/EP2017/075851
§ 371 (c)(1),
(2) Date: Mar. 20, 2019

(87) PCT Pub. No.: WO2018/069345
PCT Pub. Date: Apr. 19, 2018

(65) Prior Publication Data
US 2019/0278972 A1 Sep. 12, 2019

(30) Foreign Application Priority Data
Oct. 11, 2016 (JP) .............................. JP2016-200481

(51) Int. Cl.
*G06K 9/00* (2006.01)
*A61B 3/00* (2006.01)
(Continued)

(52) U.S. Cl.
CPC .......... *G06K 9/0061* (2013.01); *A61B 3/0025* (2013.01); *A61B 3/102* (2013.01);
(Continued)

(58) Field of Classification Search
CPC ................ G06K 9/0061; G06T 7/0012; G06T 2207/30041; G06F 3/013; A61B 3/102;
(Continued)

(56) References Cited

U.S. PATENT DOCUMENTS 5,815,242 A 9/1998 Anderson et al.
5,889,576 A 3/1999 Fujieda
(Continued)

FOREIGN PATENT DOCUMENTS

EP 3 001 943 A1 4/2016
EP 3001943 A1 4/2016
(Continued)

OTHER PUBLICATIONS

M. S. Haleem et al.: "Retinal Area Detector From Scanning Laser Ophthalmoscope (SLO) Images for Diagnosing Retinal Diseases," IEEE Journal of Biomedical and Health Informatics, vol. 19, No. 4, Jul. 2015, pp. 1472-1482.
(Continued)

*Primary Examiner* — Jerome Grant, II
(74) *Attorney, Agent, or Firm* — Delucia, Mlynar & Alicandro LLP

(57) ABSTRACT

There is provided an ocular image capturing device comprising an ocular image generating module operable to generate an image of a subject's eye based on light reflected from the eye, and a determination module arranged to determine whether or not at least a portion of a pupil region of the generated image is within a predetermined permissible region within the generated image, and to generate a signal that is indicative of the determination, the pupil region being an image of at least a portion of the pupil of the eye.

15 Claims, 18 Drawing Sheets

(51) Int. Cl.
   *A61B 3/14*    (2006.01)
   *G06F 3/01*    (2006.01)
   *A61B 3/10*    (2006.01)
   *G06T 7/00*    (2017.01)
   *A61B 3/15*    (2006.01)

(52) U.S. Cl.
   CPC ............ *A61B 3/1025* (2013.01); *A61B 3/145* (2013.01); *A61B 3/152* (2013.01); *G06F 3/013* (2013.01); *G06T 7/0012* (2013.01); *G06T 2207/30041* (2013.01)

(58) Field of Classification Search
   CPC ..... A61B 3/1025; A61B 3/152; A61B 3/0025; A61B 3/145
   USPC .......................................................... 382/117
   See application file for complete search history.

(56) References Cited

U.S. PATENT DOCUMENTS

| | | | |
|---|---|---|---|
| 7,959,290 B2 | 6/2011 | Cairns et al. | |
| 9,355,315 B2* | 5/2016 | Vugdelija | G06K 9/00604 |
| 10,692,210 B2* | 6/2020 | Ishii | G06K 9/4604 |
| 2005/0105049 A1 | 5/2005 | Maeda | |
| 2010/0149489 A1 | 6/2010 | Kikawa et al. | |
| 2013/0135583 A1 | 5/2013 | Gray et al. | |
| 2013/0195336 A1 | 8/2013 | Uchida | |
| 2013/0335703 A1 | 12/2013 | Creasey et al. | |
| 2014/0253686 A1 | 7/2014 | Wong et al. | |
| 2014/0320809 A1 | 10/2014 | Fukuma et al. | |
| 2014/0327882 A1 | 11/2014 | Muyo et al. | |
| 2015/0097925 A1* | 4/2015 | Choo | G06K 9/00604 |
| | | | 348/40 |
| 2015/0164319 A1* | 6/2015 | Kim | G06K 9/0061 |
| | | | 351/210 |
| 2015/0216408 A1 | 8/2015 | Brown et al. | |
| 2016/0235299 A1 | 8/2016 | Yamamoto et al. | |
| 2017/0258327 A1 | 9/2017 | Wada et al. | |
| 2018/0239427 A1* | 8/2018 | Hakoshima | G06T 7/73 |
| 2018/0335839 A1* | 11/2018 | Lin | G06K 9/036 |
| 2019/0222830 A1* | 7/2019 | Edwin | G06F 3/013 |
| 2019/0294858 A1* | 9/2019 | Creedon | A61B 3/12 |
| 2019/0324550 A1* | 10/2019 | Liao | G06F 3/013 |
| 2020/0111259 A1* | 4/2020 | Sears | G06F 3/012 |
| 2020/0245867 A1* | 8/2020 | Pascal | A61B 3/102 |
| 2020/0278539 A1* | 9/2020 | Petljanski | G02B 27/0101 |

FOREIGN PATENT DOCUMENTS

| | | |
|---|---|---|
| JP | 3490088 B2 | 1/2004 |
| JP | 2005 342282 A | 12/2005 |
| JP | 4971872 A | 7/2012 |
| JP | 5330236 B2 | 10/2013 |
| JP | 2014 200679 A | 10/2014 |
| JP | 2015-534482 A | 12/2015 |
| JP | 2016 510628 A | 4/2016 |
| JP | 2016 067795 A | 5/2016 |
| JP | 2016 105945 A | 6/2016 |
| JP | 2016 150032 A | 8/2016 |
| WO | 95/13012 A2 | 5/1995 |
| WO | 2008/009877 A1 | 1/2008 |
| WO | WO 2014 158 263 A1 | 10/2014 |

OTHER PUBLICATIONS

Japanese Office Action Issued in Japanese Application No. 2019-515970, dated Jun. 16, 2020. [English Translation of Japanese Office Action Attached].

Int'l Search Report and Written Opinion from Int'l Appl'n No. PCT/EP2017/075851, dated Dec. 12, 2017.

\* cited by examiner

OCULAR IMAGE CAPTURING DEVICE

This application is a National Stage Application of International Application No. PCT/EP2017/075851, filed 10 Oct. 2017, which claims benefit of Serial No. 2016-200481, filed 11 Oct. 2016 in Japan and which applications are incorporated herein by reference. To the extent appropriate, a claim of priority is made to each of the above disclosed applications.

TECHNICAL FIELD

Technology disclosed herein relates to an ocular image capturing device, an ocular image processing method, and an ocular image processing program.

BACKGROUND

For convenience of explanation, optical coherence tomography is referred to as "OCT" and scanning laser ophthalmoscopy is referred to as "SLO" hereafter.

Patent Document 1 describes an ocular fundus examination device provided with an OCT unit that generates an image using OCT. In the OCT unit described by Patent Document 1, a tomographic image that is an image taken in the thickness direction of the membrane of the ocular fundus of a subject's eye is generated based on an image signal detected by charge coupled devices (CCDs).

A liquid crystal display (LCD) is housed in the ocular fundus examination device of Patent Document 1, and the LCD displays a fixation target to cause the gaze of the subject's eye to be fixed in a specific orientation in a case in which the ocular fundus is imaged by the OCT unit. Light from the LCD is incident to the subject's eye via an optical system that includes lenses and mirrors, such that the fixation target is projected onto the ocular fundus of the subject's eye.

Moreover, a system that combines SLO and OCT is described in Patent Document 2. Moreover, emitting visible light onto the anterior segment of the subject's eye from an oblique direction and aligning imaging in OCT based on reflected light from the anterior segment is described in Patent Document 2.

RELATED DOCUMENTS

Related Patent Documents

Patent Document 1: Japanese Patent Number 4971872
Patent Document 2: Japanese National-Phase Publication No. 2015-534482

SUMMARY OF INVENTION

However, in the technology described by Patent Document 2, alignment sometimes cannot be performed with high precision in a case in which capturing an ocular image since alignment of the imaging is performed based on reflected light from the anterior segment of the subject's eye.

An ocular image capturing device according to a first aspect of the present invention comprises an ocular image generating module operable to generate an image of a subject's eye based on light reflected from the eye, and a determination module arranged to determine whether or not at least a portion of a pupil region of the generated image is within a predetermined permissible region within the generated image, and to generate an output signal that is indicative of the determination, the pupil region being an image of at least a portion of the pupil of the eye.

An ocular image capturing device according to a second aspect of the present invention comprises: an ocular image generating module operable to generate an image of a subject's eye based on light reflected from the eye; and a determination module arranged to determine whether or not a proportion of a predetermined permissible region of the generated image that is occupied by at least a portion of a pupil region of the generated image is a predetermined threshold value or greater, and to generate an output signal that is indicative of the determination, the pupil region being an image of at least a portion of the pupil of the eye.

In an embodiment of the ocular image capturing device according to the first or second aspect, the ocular image generating module may comprise: an ocular image capturing module arranged to capture an image of the subject's eye based on light reflected from the eye; and a determination-use image generating module arranged to generate a determination-use image by removing from the captured image an unneeded region other than a captured image pupil region, the captured image pupil region being an image of at least a portion of the pupil in the captured image. In this case, the determination module may be arranged to perform the determination based on the determination-use image.

In an embodiment of the ocular image capturing device according to the first or second aspect, the ocular image generating module may comprise: an ocular image capturing module arranged to capture an image of the subject's eye based on light reflected from the eye; a binary image generation module arranged to generate a binary image by binarizing the captured image; and a determination-use image generating module arranged to generate a determination-use image by removing from the binary image an unneeded region other than a binary image pupil region, the binary image pupil region being an image of at least a portion of the pupil in the binary image. In this case, the determination module may be arranged to perform the determination based on the determination-use image.

Any of the ocular image capturing devices set our above may further comprise an illumination module arranged to illuminate the ocular fundus of the subject's eye, wherein the ocular image generating module comprises an ocular image capturing module arranged to capture an image of the subject's eye based on light reflected from the eye, and a field-of-view of the illumination module has a predetermined relationship to a field-of-view of the ocular image capturing module. In this case, the ocular image capturing device may further comprise a controller arranged to control the illumination module based on the output signal generated by the determination module. Furthermore, the determination module may be arranged to repeatedly perform the determination while the illumination module is illuminating the ocular fundus, the ocular image capturing device further comprising a storage module arranged to store the results of the determinations performed by the determination module. Further still, the illumination module may comprise a tomographic image acquisition module arranged to acquire a tomographic image of the ocular fundus of the subject's eye using interference, from light that has been emitted toward the subject's eye, between reflected light from the ocular fundus of the subject's eye and reference light that has passed along an optical pathway different from the optical pathway of the reflected light.

The ocular image capturing device according to the first or second aspect, or either of the embodiments thereof set out above, may further comprise: a tomographic image acquisition module arranged to acquire a tomographic image of the ocular fundus of the subject's eye using interference, from light that has been emitted toward the subject's eye, between reflected light from the ocular fundus of the subject's eye and reference light that has passed along an optical pathway different from the optical pathway of the reflected light; and a control module arranged to control acquisition of the tomographic image by the tomographic image acquisition module based on the determination performed by the determination module. In this case, the ocular image generating module may comprise: a first light source arranged to emit light for imaging the ocular fundus; a first scanning optical system arranged to scan light in a first direction and that scans light in an ultra-wide field in a second direction intersecting the first direction; and a first optical receiver arranged to receive light from the ocular fundus of the subject's eye in a case in which the subject's eye has been scanned by the first scanning optical system using light emitted from the first light source, wherein the tomographic image acquisition module includes: a second light source arranged to emit light for generating a tomographic image; a second scanning optical system arranged to scan light in the first direction and that scans light in an ultra-wide field in the second direction; a second optical receiver arranged to receive, from light emitted from the second light source by the second scanning optical system, reflected light from the ocular fundus of the subject's eye and reference light that has passed along an optical pathway different from the optical pathway of the reflected light; and a generating module arranged to generate the tomographic image based on the reflected light and the reference light received by the second optical receiver.

Any of the ocular image capturing devices set our above may further comprise: a fixation target display module arranged to display a fixation target for fixing the gaze of the subject's eye; and a fixation target display controller arranged to control at least one characteristic of the displayed fixation target based on the output signal generated by the determination module.

Any of the ocular image capturing devices set our above may further comprise: a display; and a display controller arranged to set a display content of the display based on the output signal generated by the determination module.

An ocular image processing method according to a third aspect of the present invention comprises: acquiring an image of a subject's eye based on light reflected from the eye; determining whether or not at least a portion of a pupil region of the acquired image is within a predetermined permissible region within the acquired image, the pupil region being an image of at least a portion of the pupil of the eye; and generating an output signal that is indicative of the determination.

An ocular image processing method according to a fourth aspect of the present invention comprises: acquiring an image of a subject's eye based on light reflected from the eye; determining whether or not a proportion of a predetermined permissible region of the acquired image that is occupied by at least a portion of a pupil region of the acquired image is a predetermined threshold value or greater, the pupil region being an image of at least a portion of the pupil of the eye; and generating an output signal that is indicative of the determination.

A non-transitory storage medium according to a fifth aspect of the invention stores computer program instructions which, when executed by a processor, cause the processor to perform at least one of the methods set out above.

BRIEF DESCRIPTION OF DRAWINGS

FIG. 15 (B) is a diagram illustrating a first modified example of the scanning optical system of FIG. 15 (A).

FIG. 15 (C) is a diagram illustrating a second modified example of the scanning optical system of FIG. 15 (A).

DESCRIPTION OF EMBODIMENTS

Figure 1:
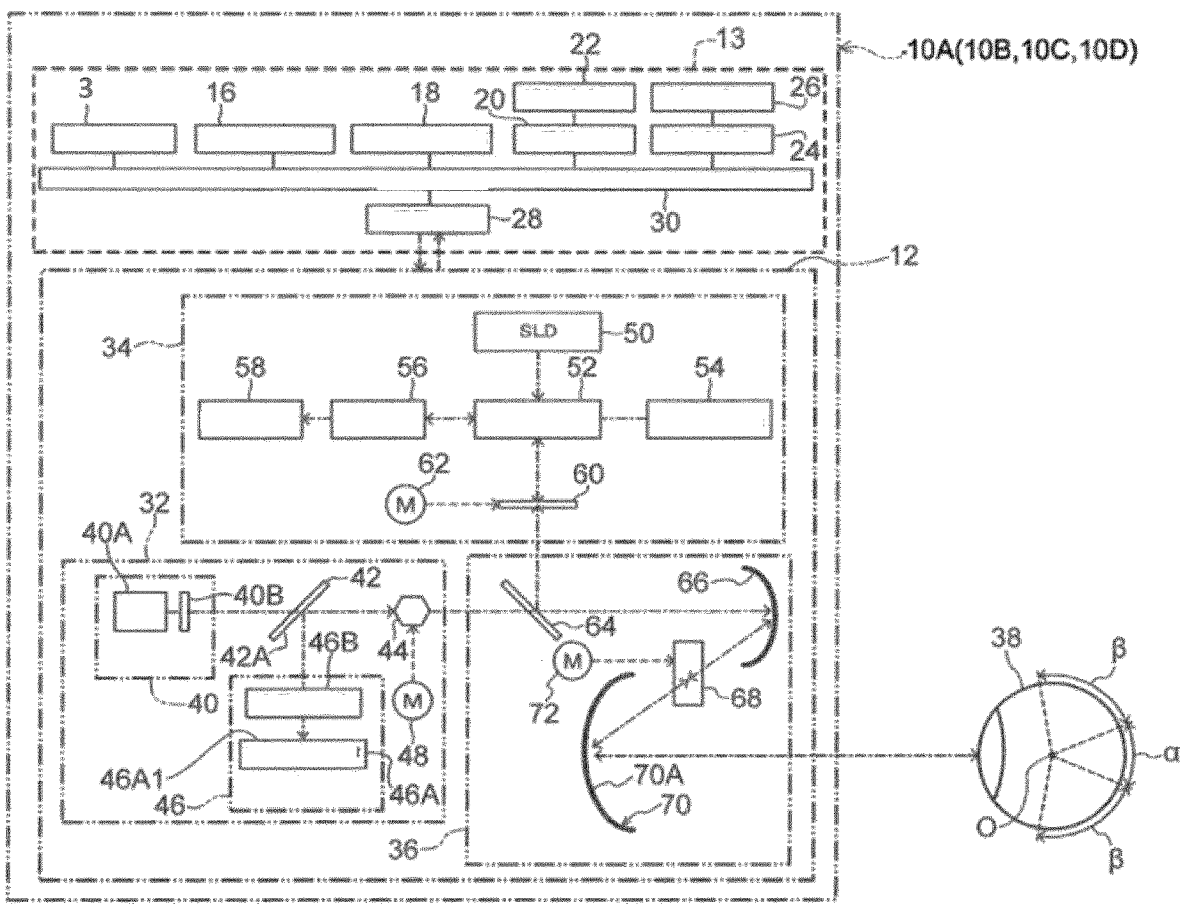
FIG. 1 is a block diagram illustrating an example of an overall configuration of an ocular image capturing device.

There is described in the following an ocular image capturing device and an ocular image capturing method that are capable of aligning capturing of an ocular image with high precision.

More particularly, there is described an ocular image capturing device which includes an ocular fundus image capturing module that captures an ocular fundus image based on light reflected from an ocular fundus of a subject's eye; and a determination module that determines whether or not the position of the pupil of the subject's eye is within a predetermined permissible range based on the ocular fundus image captured by the ocular fundus image capturing module.

The determination module may include: a binary image generation module that generates a binary image by binarizing the ocular fundus image; and a determination-use image generating module that generates a determination-use image by removing an unneeded region other than the pupil from the binary image, wherein whether or not the position of the pupil of the subject's eye is within a predetermined permissible range is determined based on the determination-use image.

The determination module may determine that the position of the pupil of the subject's eye is within the permissible range in a case in which a ratio of a region occupied by the pupil to a predetermined determination region of the determination-use image is a predetermined threshold value or greater.

The ocular image capturing device may further include a tomographic image acquisition module that acquires a tomographic image of the ocular fundus of the subject's eye using interference, from light that has been emitted toward the subject's eye, between reflected light from the ocular fundus of the subject's eye and reference light that has passed along an optical pathway different from the optical pathway of the reflected light; and a control module that controls acquisition of the tomographic image by the tomographic image acquisition module based on the determination result by the determination module.

The ocular fundus image capturing module may include: a first light source that emits light for imaging the ocular fundus; a first scanning optical system that scans light in a first direction and that scans light in an ultra-wide field in a second direction intersecting the first direction; and a first optical receiver that receives light from the ocular fundus of the subject's eye in a case in which the subject's eye has been scanned by the first scanning optical system using light emitted from the first light source, wherein the tomographic image acquisition module includes: a second light source that emits light for generating a tomographic image; a second scanning optical system that scans light in the first direction and that scans light in an ultra-wide field in the second direction; a second optical receiver that receives, from light emitted from the second light source by the second scanning optical system, reflected light from the ocular fundus of the subject's eye and reference light that has passed along an optical pathway different from the optical pathway of the reflected light; and a generating module that generates the tomographic image based on the reflected light and the reference light received by the second optical receiver.

An ocular fundus examination method described herein includes an ocular fundus image capturing step of capturing an ocular fundus image based on light reflected from an ocular fundus of a subject's eye; and a determination step of determining whether or not the position of the pupil of the subject's eye is within a predetermined permissible range based on the ocular fundus image captured by the ocular fundus image capturing step.

An ocular fundus examination program described herein causes a computer to execute processing, the processing comprising: an ocular fundus image capturing step of capturing an ocular fundus image based on light reflected from the ocular fundus of a subject's eye; and a determination step of determining whether or not the position of the pupil of the subject's eye is within a predetermined permissible range based on the ocular fundus image captured by the ocular fundus image capturing step.

One exemplary embodiment of the present invention has an advantageous effect of enabling alignment of capturing of ocular fundus images to be performed with high precision.

Explanation follows regarding exemplary embodiments according to the present invention, with reference to the attached drawings.

Note that in the exemplary embodiments, "perpendicular" denotes perpendicular with the meaning encompassing error within a permitted range, and "parallel" denotes parallel with the meaning encompassing error within a permitted range. Moreover, in the exemplary embodiments, "facing" denotes facing with the meaning encompassing error within a permitted range. Moreover, in the exemplary embodiments, "the same" denotes the same with the meaning encompassing error within a permitted range.

For convenience of explanation in the exemplary embodiments, super luminescent diode is denoted "SLD". For convenience of explanation in the exemplary embodiments, interface is denoted "I/F". In the exemplary embodiments, red is denoted "R" and green is denoted "G".

As illustrated as an example in FIG. 1, an ocular image capturing device 10 (which may be used as an ocular fundus examination device) includes a device main body 12 and a controller 13.

The device main body 12 comprises an ocular image generating module that is operable to generate an image of a subject's eye 38 based on light reflected from the eye 38. The ocular image generating module comprises an ocular image capturing module arranged to capture an image of the eye 38 based on the light reflected from the eye 38, which may, as in the present embodiment, comprise an SLO unit 32.

The device main body may, as in the present embodiment, further comprise an illumination module arranged to illuminate the ocular fundus of the subject's eye 38 (for example, with light of wavelengths that are suitable for treatment of the retina), wherein a field-of-view of the illumination module has a predetermined relationship to a field-of-view of the ocular image capturing module. The illumination module may function not only to illuminate the ocular fundus of the subject's eye 38 but also image the illuminated part of the ocular fundus. The illumination module may, as in the present embodiment, comprise a tomographic image acquisition module comprising an OCT unit 34, which is arranged to acquire a tomographic image of the ocular fundus of the subject's eye 38 using interference, from light that has been emitted toward the subject's eye 38, between reflected light from the ocular fundus of the subject's eye 38 and reference light that has passed along an optical pathway different from the optical pathway of the reflected light. Further details of the tomographic image acquisition module are provided below.

As illustrated in FIG. 1, the device main body 12 includes the SLO unit 32, the OCT unit 34, and a shared optical system 36.

The ocular image capturing device 10 thus includes SLO imaging system functionality, which is functionality for imaging using SLO, and OCT imaging system functionality, which is functionality for imaging using OCT. The functionality of the SLO imaging system (as an example of the aforementioned ocular image generating module) is implemented by the controller 13, the SLO unit 32, and the shared optical system 36. The functionality of the OCT imaging system (as an example of the aforementioned illumination module) is implemented by the controller 13, the OCT unit 34, and the shared optical system 36.

The ocular image capturing device 10 includes an SLO mode, which is an operation mode that exercises the SLO imaging system functionality, and an OCT mode, which is an operation mode that exercises the OCT imaging system functionality. The SLO mode and the OCT mode are selectively set according to user instructions or sequence control.

The SLO unit 32 includes an emission section 40, a beam splitter 42, a polygon mirror 44, a photo detector 46, and a motor 48, that are employed to generate a two-dimensional image of the surface of the ocular fundus of a subject's eye 38.

The ocular fundus of the subject's eye 38 is simply denoted the "ocular fundus" hereafter for convenience of explanation. Hereafter, in cases in which, for example, the ocular image capturing device 10 is installed on a horizontal surface, a direction substantially perpendicular to the horizontal surface (not illustrated in the drawings) is denoted the "Y direction" for convenience of explanation. For example, a direction that is substantially parallel to a horizontal surface and that is the depth direction of the subject's eye 38 positioned in a state in which the anterior segment is facing an eyepiece lens (not illustrated in the drawings) of the ocular image capturing device 10, in a case in which the ocular image capturing device 10 is installed on the horizontal surface, is denoted the "Z direction" hereafter for convenience of explanation. Hereafter, a direction substantially perpendicular to both the Y direction and the Z direction is denoted the "X direction" hereafter for convenience of explanation.

The emission section 40 includes a light source 40A and a bandpass filter 40B. The light source 40A is a light source for imaging using SLO, and emits light having a wavelength in a range of from approximately 400 nanometers to approximately 1100 nanometers. Light emitted from the light source 40A passes through the bandpass filter 40B such that only light having specific wavelengths is emitted onto the beam splitter 42.

In the present first exemplary embodiment, light emitted from the emission section 40 is broadly split into visible RG light and near-infrared light, which is light having a wavelength in the near-infrared region.

In the present first exemplary embodiment, RG light and near-infrared light are selectively emitted from the emission section 40 by varying the wavelength of the light produced by the light source 40A, and by applying the bandpass filter 40B to the light produced by the light source 40A.

For convenience of explanation, RG light and near-infrared light, serving as the light emitted from the emission section 40, are simply referred to as "SLO light" hereafter in a case in which explanation does not need to distinguish between the two.

The beam splitter 42 guides the SLO light to the polygon mirror 44 by transmitting the SLO light, and guides first ocular fundus reflected light to the photo detector 46. Here, first ocular fundus reflected light denotes light reflected by the ocular fundus originating from the SLO light. Light reflected by the ocular fundus denotes light that was reflected by the ocular fundus and was then incident to the shared optical system 36.

The polygon mirror 44 sends the SLO light from the beam splitter 42 to the shared optical system 36. Then, as illustrated as an example in FIG. 2, the polygon mirror 44 scans the SLO light in the Y direction by rotating in the arrow A direction on receiving drive force of the motor 48.

The photo detector 46 includes a photo detector 46A and an optical filter 46B. The optical filter 46B is disposed at a position between an optical reception face 46A1 of the photo detector 46A and a reflecting face 42A of the beam splitter 42, and covers an optical reception face 46A1. First ocular fundus reflected light made of near-infrared light and first ocular fundus reflected light made of RG light are selectively made incident to the optical reception face 46A1.

The photo detector 46A generates an SLO image signal, which is an image signal based on the first ocular fundus reflected light that was incident via the optical filter 46B, and outputs the generated SLO image signal.

The OCT unit 34 is employed to generate a tomographic image of the ocular fundus, and includes an SLD 50, an optical coupler 52, a reference light optical system 54, a spectrophotometer 56, a line sensor 58, a V-galvanometer mirror 60, and a motor 62.

The SLD 50 emits low-coherence light. Low-coherence light, for example, denotes light encompassing light in the near-infrared region having a longer wavelength than near-infrared light emitted from the emission section 40 and having a time-wise coherence length of approximately several tens of micrometers.

Low-coherence light emitted from the SLD 50 is fed into the optical coupler 52 via a first optical fiber (not illustrated in the drawings) and is split into reference light and signal light. The reference light is guided to the reference light optical system 54 via a second optical fiber (not illustrated in the drawings), and the signal light is guided to the V-galvanometer mirror 60 via a third optical fiber (not illustrated in the drawings).

The reference light optical system 54 is an optical delay line which matches the optical path length between the eye 38 and the optical coupler 52.

The reference mirror returns reference light to the optical coupler 52 via the same optical path by reflecting the reference light. The reference mirror is a movable mirror that can move in the direction of the optical axis of the reference light, and the length of the optical path of the reference light is adjusted by moving the position of the reference mirror on the optical axis.

The V-galvanometer mirror 60 sends signal light to the shared optical system 36. Then, as illustrated as an example in FIG. 2, the V-galvanometer mirror 60 scans the signal light in the Y direction by rotationally oscillating in the arrow B direction on receiving drive force of the motor 62.

Moreover, the V-galvanometer mirror 60 guides second ocular fundus reflected light to the optical coupler 52 via a fourth optical fiber. Here, the second ocular fundus reflected light denotes light reflected by the ocular fundus originating from signal light.

The second ocular fundus reflected light guided by the optical coupler 52 is superimposed with the reference light guided from the reference light optical system to the optical coupler 52 by the optical coupler 52 and interference occurs. Interference light obtained due to the interference occurring is spectrally dispersed by the spectrophotometer 56, and the spectrally dispersed interference light is guided to the line sensor 58.

The line sensor 58 generates an OCT image signal, which is an image signal based on incident interference light, and outputs the generated OCT image signal.

The shared optical system 36 includes a dichroic mirror 64, a slit mirror 66 that has an elliptical, concave reflecting face, an H-galvanometer mirror 68, an ellipsoid mirror 70, and a motor 72.

The dichroic mirror 64 guides the SLO light to the slit mirror 66 by causing the SLO light from the polygon mirror 44 of the SLO unit 32 to be transmitted, and guides the signal light to the slit mirror 66 by causing the signal light from the V-galvanometer mirror 60 of the OCT unit 34 to be reflected.

For convenience of explanation, signal light and SLO light are denoted "emitted light" hereafter in a case in which there is no need for the explanation to distinguish between the two.

Figure 2:
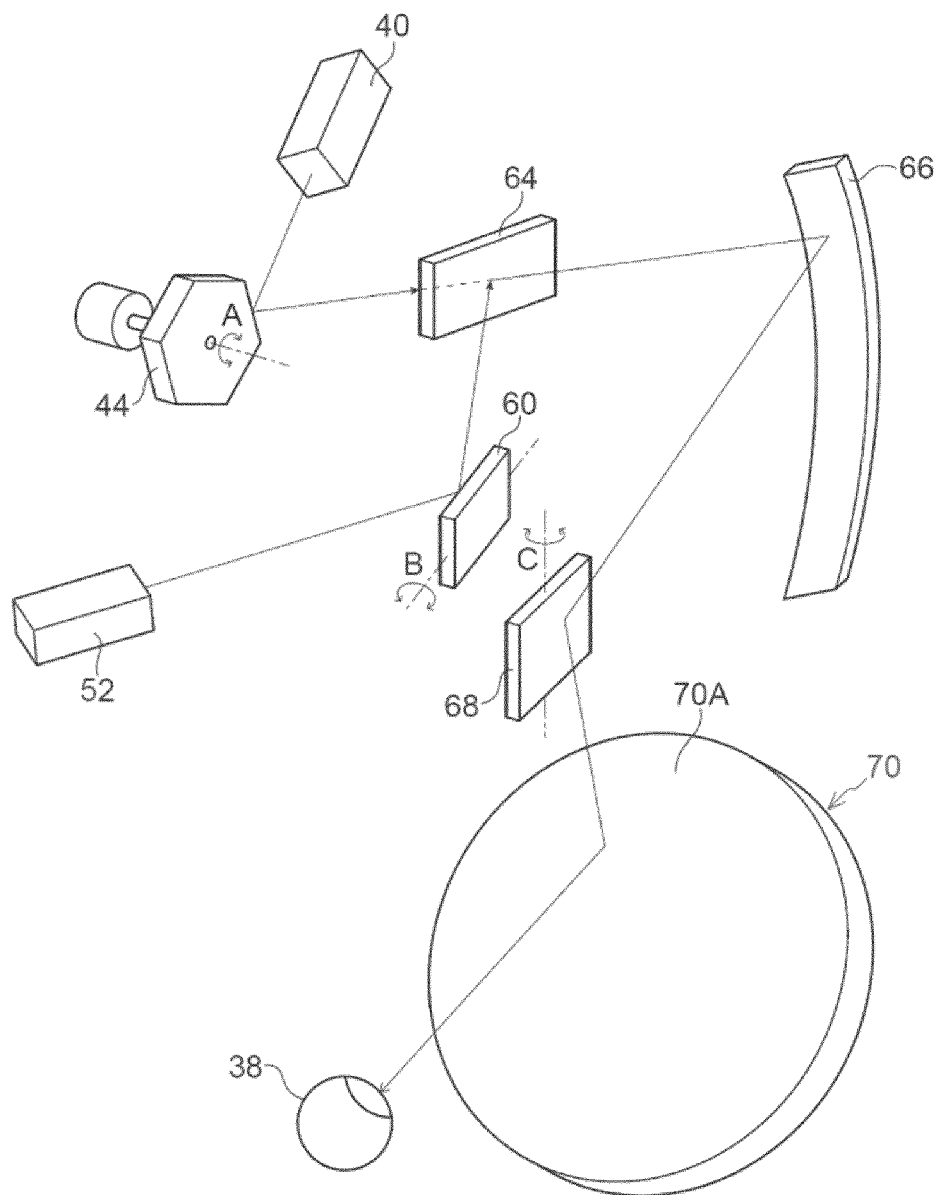
FIG. 2 is a schematic perspective view illustrating an example of a configuration of an optical system that guides light emitted from respective light sources of an imaging system of an ocular image capturing device to a subject's eye.

The slit mirror 66 reflects incident emitted light toward the H-galvanometer mirror 68. The H-galvanometer mirror 68 reflects and sends the emitted light from the slit mirror 66 to a mirror face 70A of the ellipsoid mirror 70. Then, as illustrated in the example of FIG. 2, the H-galvanometer mirror 68 scans the emitted light in an X direction by rotationally oscillating in the arrow C direction on receiving drive force from the motor 48.

The ellipsoid mirror 70 guides emitted light to the ocular fundus by reflecting emitted light that was incident to the mirror face 70A. The ellipsoid mirror 70 is disposed such that a focal point based on the emitted light reflected by the mirror face 70A is positioned at the subject's eye 38. Emitted light guided to the ocular fundus by the ellipsoid mirror 70 is reflected by the ocular fundus. Then, the ocular fundus reflected light is guided to the dichroic mirror 64 in the shared optical system 36, following the same optical pathway as the emitted light. The dichroic mirror 64 guides the first ocular fundus reflected light to the SLO unit 32 and guides the second ocular fundus reflected light to the OCT unit 34. Basic configuration of an ocular fundus imaging optical system configured by two elliptical faces is similar to the configurations described in PCT application No. PCT/GB94/02465 (WO 95/13012) and PCT application No. PCT/GB2007/002208 (WO 2008/009877), the disclosures of each of which are incorporated herein by reference in their entirety. Further, the embodiments herein can be combined, both structurally and operationally, with the technically-related systems and methodologies disclosed in, for example, U.S. Pat. No. 7,959,290, US 2015/0216408, US 2014/0327882, US 2013/0135583, and US 2013/0335703, the disclosures of each of which are also incorporated herein by reference in their entirety.

Note that in the ocular image capturing device 10, the region that light is emitted onto on the ocular fundus is broadly split into a first emitted-onto region α and a second emitted-onto region β as illustrated as an example in FIG. 1. First emitted-onto region α denotes, for example, an angle range on the Z direction side of 45° about the center O of the subject's eye 38, in other words, a region spreading out along the circumferential direction of the ocular fundus from the center of the ocular fundus at an angle of 45°, with the center O of the subject's eye 38 as a reference point. Second emitted-onto region β denotes, for example, an angle range on the Z direction side of more than 45° but no more than 200° about the center O of the subject's eye 38, in other words, a region spreading out over an angle range of more than 45° but no more than 200° from the center of the ocular fundus along the circumferential direction of the ocular fundus, with the center O of the subject's eye 38.

The controller 13 controls operation of the device main body 12 by exchanging a variety of information with the device main body 12. Moreover, the controller 13 generates a two-dimensional image indicating an aspect of the surface of the ocular fundus based on the SLO image signal obtained from the photo detector 46A. The controller 13 may, as part of the ocular image generating module, also perform image processing operations described herein below on captured ocular images to generate images of the subject's eye 38 for processing by the determination module described below. The controller 13 also generates a tomographic image of the ocular fundus based on the OCT image signal obtained from the line sensor 58.

Note that in this first exemplary embodiment, the two-dimensional image obtained using the SLO unit 32 is broadly split into a chromatic image based on RG light and an achromatic image based on near-infrared light. Moreover, tomographic images obtained using the OCT unit 34 are achromatic images. Two-dimensional images obtained using the SLO unit 32 and the tomographic image obtained using the OCT unit 34 may be displayed as still images, or may be displayed as a live view image.

The controller 13 includes a primary controller 14, an OCT image generator 16, an SLO image generator 18, a reception I/F 20, a reception device 22, a display controller 24, a display 26, a communication I/F 28, and a bus line 30.

The primary controller 14, the OCT image generator 16, the SLO image generator 18, the reception I/F 20, the display controller 24, and the communication I/F 28 are connected to one another by the bus line 30. Accordingly, the primary controller 14 can exchange various items of information with the OCT image generator 16, the SLO image generator 18, the reception I/F 20, the display controller 24, and the communication I/F 28.

The primary controller 14 controls driving of the motors 48, 62, 72 by controlling respective motor drive circuits (not illustrated in the drawings) corresponding to the motors 48, 62, 72 via the communication I/F 28.

Moreover, the primary controller 14 switches between lighting-up and lighting-out the light source 40A, adjusts the amount of light, changes the wavelength of light produced by the light source 40A, and the like, by controlling a light source drive circuit (not illustrated in the drawings) corresponding to the light source 40A via the communication I/F 28.

Moreover, the primary controller 14 switches between lighting-up and lighting-out the SLD 50, adjusts the amount of light, changes the wavelength of light produced by the SLD 50, and the like, by controlling a SLD drive circuit (not illustrated in the drawings) corresponding to the SLD 50 via the communication I/F 28.

Moreover, the primary controller 14 controls operation of the bandpass filter 40B, operation of the optical filter 46B, and operation of the reference mirror of the reference light optical system 54 via the communication I/F 28.

The reception device 22 includes a keyboard, a mouse, a touch panel, or the like, and receives various instructions from a user.

The reception device 22 is connected to the reception I/F 20 and outputs an instruction content signal indicating contents of the received instructions to the reception I/F 20. The primary controller 14 executes processing in accordance with the instruction content signal input from the reception I/F 20.

The display 26 is, for example, an LCD or organic electroluminescence display (OELD). The display 26 is connected to the display controller 24. Under control by the primary controller 14, the display controller 24 controls the display 26 so as to display on the display 26 a two-dimensional image obtained using the SLO unit 32 and a tomographic image obtained using the OCT unit 34, as still images or a live view image. Under control by the primary controller 14, the display controller 24 also displays various screens, such as menu screens, by controlling the display 26.

The communication I/F 28 is connected to an electrical system of a device main body 12, and operates under control by the primary controller 14 to govern exchange of various information between the primary controller 14 and the device main body 12.

The SLO image generator 18 acquires the SLO image signal from the photo detector 46A of the SLO unit 32 via the communication I/F 28, and is a dedicated circuit that performs processing to generate a two-dimensional image based on the acquired SLO image signal.

The SLO image generator 18, for example, outputs each frame of the generated two-dimensional images to the display controller 24 at a specific frame rate of typically tens of frames per second. The display controller 24 displays the two-dimensional images input from the SLO image generator 18 on the display 26 as a live image in accordance with instructions by the primary controller 14. Moreover, the display controller 24 displays the two-dimensional images input from the SLO image generator 18 on the display 26 as still images, in accordance with instructions by the primary controller 14.

The OCT image generator 16 acquires the OCT image signal from the line sensor 58 of the OCT unit 34 via the communication I/F 28, and is a dedicated circuit that performs processing to generate a tomographic image based on the acquired OCT image signal.

The OCT image generator 16, for example, outputs each frame of the generated tomographic images to the display controller 24 at a specific frame rate of typically tens of frames per second. The display controller 24 displays the tomographic images input from the OCT image generator 16 on the display 26 as a live view image in accordance with instructions by the primary controller 14. Moreover, the display controller 24 displays the tomographic images input from the OCT image generator 16 on the display 26 as still images, in accordance with instructions by the primary controller 14.

Note that in this first exemplary embodiment, an example is given in which the OCT image generator 16 and the SLO image generator 18 are each implemented by a computer that includes a CPU, ROM, and RAM. However, technology disclosed herein is not limited thereto. For example, the OCT image generator 16 and the SLO image generator 18 may each be implemented by a computer that includes a CPU, ROM, and RAM, or may be implemented by an application specific integrated circuit (ASIC). Moreover, the OCT image generator 16 and the SLO image generator 18 may each be implemented by field-programmable gate arrays (FPGA), or a combination of hardware configuration and software configuration.

Figure 3:
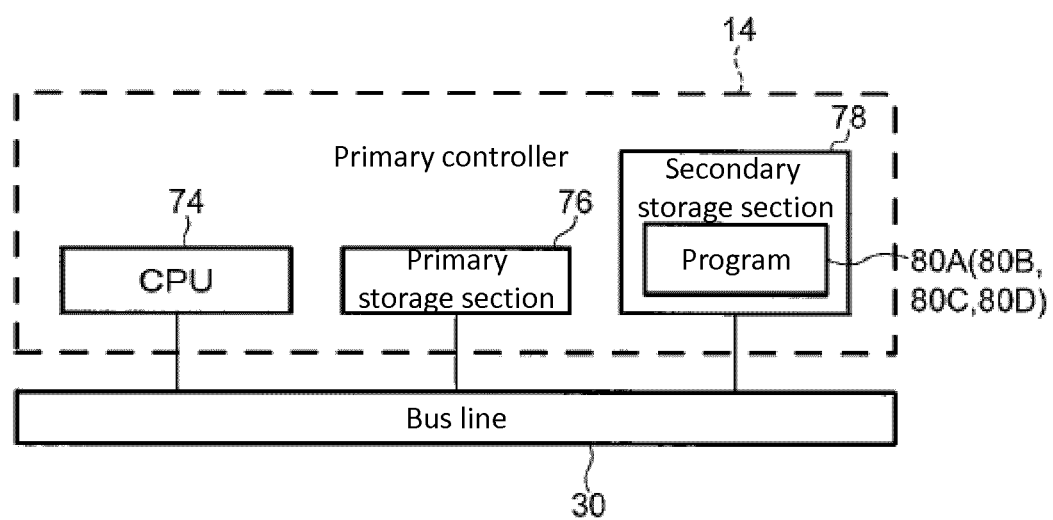
FIG. 3 is a block diagram illustrating an example of hardware configuration of a primary controller included in the ocular image capturing device.

As illustrated as an example in FIG. 3, the primary controller 14 includes a central processing unit (CPU) 74, a primary storage section 76, and a secondary storage section 78. The CPU 74, the primary storage section 76, and the secondary storage section 78 are connected to one another by the bus line 30.

The CPU 74 controls the ocular image capturing device 10 overall. The primary storage section 76 is volatile memory employed as a work area or the like when executing various programs. The primary storage section 76 may store determinations performed by the determination module described herein below. Examples of the primary storage section 76 include random access memory (RAM). The secondary storage section 78 is non-volatile memory storing programs, various parameters, and the like for controlling basic operation of the ocular image capturing device 10. Examples of the secondary storage section 78 include electrically erasable programmable read only memory (EEPROM) or flash memory.

The secondary storage section 78 stores an ocular fundus image capturing program 80 executed for implementing ocular fundus image capturing processing (including ocular image processing methods), described later.

The CPU 74 reads the ocular fundus image capturing program 80 from the secondary storage section 78, expands the ocular fundus image capturing program 80 into the primary storage section 76, and executes the ocular fundus image capturing program 80, thereby operating as the determination module according to technology disclosed herein.

Figure 4:
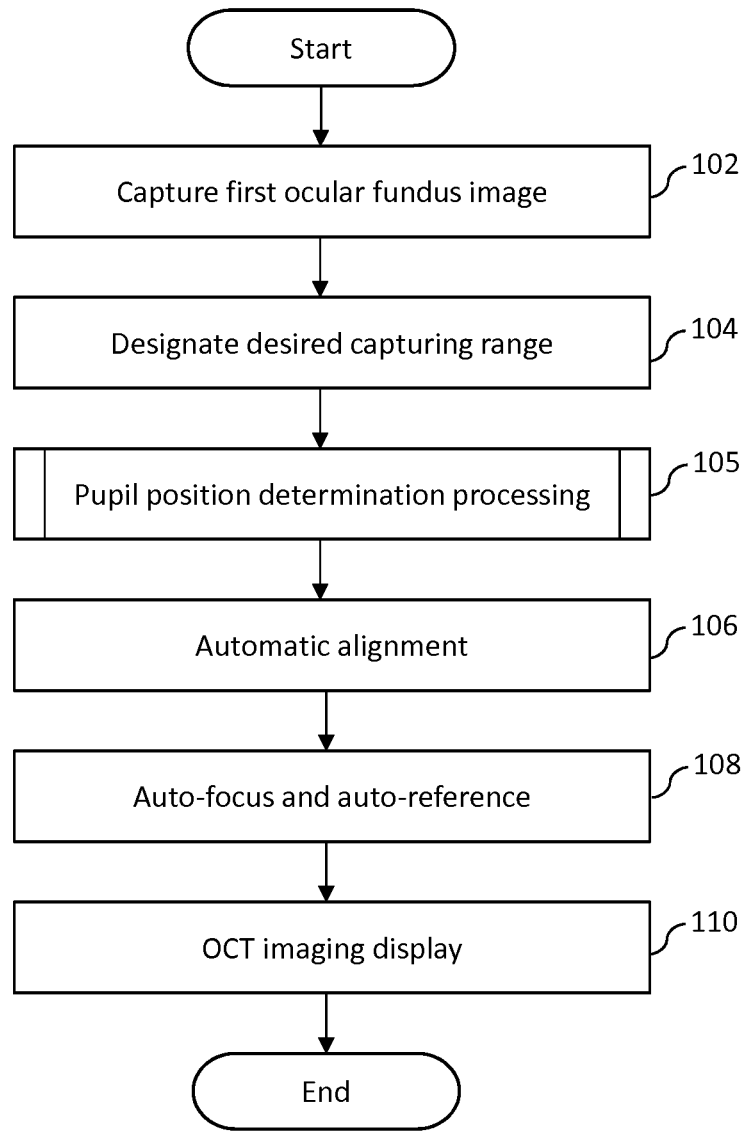
FIG. 4 is a flowchart illustrating an example of ocular fundus image capturing processing.

Next, explanation follows regarding ocular fundus image capturing processing executed by the CPU 74, with reference to the flowchart illustrated in FIG. 4. The processing illustrated in FIG. 4 is executed in a case in which the operator has operated the reception device 22 to instruct start of imaging processing.

Hereafter, RG light is emitted from the light source 40A to image the ocular fundus of the subject's eye 38 under control by the SLO unit 32, and a two-dimensional image generated by the SLO image generator 18 is referred to as an "RG-SLO image". Moreover, near-infrared light is emitted from the light source 40A to image the ocular fundus of the subject's eye 38 under control by the SLO unit 32, and a two-dimensional image generated by the SLO image generator 18 is denoted an "IR-SLO image". Moreover, low-coherence light is emitted from the SLD 50 to image the ocular fundus of the subject's eye 38 under control by the OCT unit 34, and a tomographic image generated by the OCT image generator 16 is denoted an "OCT image".

At step 102, an RG-SLO image is captured as a first ocular fundus image for the operator to designate a desired capturing range of an OCT image. More generally, the first ocular fundus image may be used by the operator to designate a desired illumination region that is to be illuminated by the illumination module. Note that explanation is given in the present exemplary embodiment regarding a case in which an RG-SLO image is captured; however, an IR-SLO image may be imaged.

First, a fixation target is displayed on a fixation target display such as an LCD (not illustrated in the drawings) in order to display a fixation target for fixing the line of sight of the subject's eye at a specific orientation. The line of sight of the subject's eye 38 is fixed at the specific orientation due to the patient looking at the fixation target.

Then, RG light is emitted from the light source 40A of the SLO unit 32, an ocular fundus image of the subject's eye 38 is captured by controlling the SLO unit 32, and an RG-SLO image is acquired from the SLO image generator 18. The acquired RG-SLO image is displayed on the display 26 as a still image.

Here, the operator refers to the still image of the RG-SLO image displayed on the display 26, and determines by sight whether or not the position of the subject's eye 38 is a position suitable for imaging. Then, in a case in which the position of the subject's eye 38 is not a position suitable for imaging, the patient is urged to look at the fixation target and re-capturing of the RG-SLO image is instructed. This is repeated until the position of the subject's eye 38 is a position suitable for imaging. At this point, the patient momentarily moves away from the device and waits.

Figure 5:
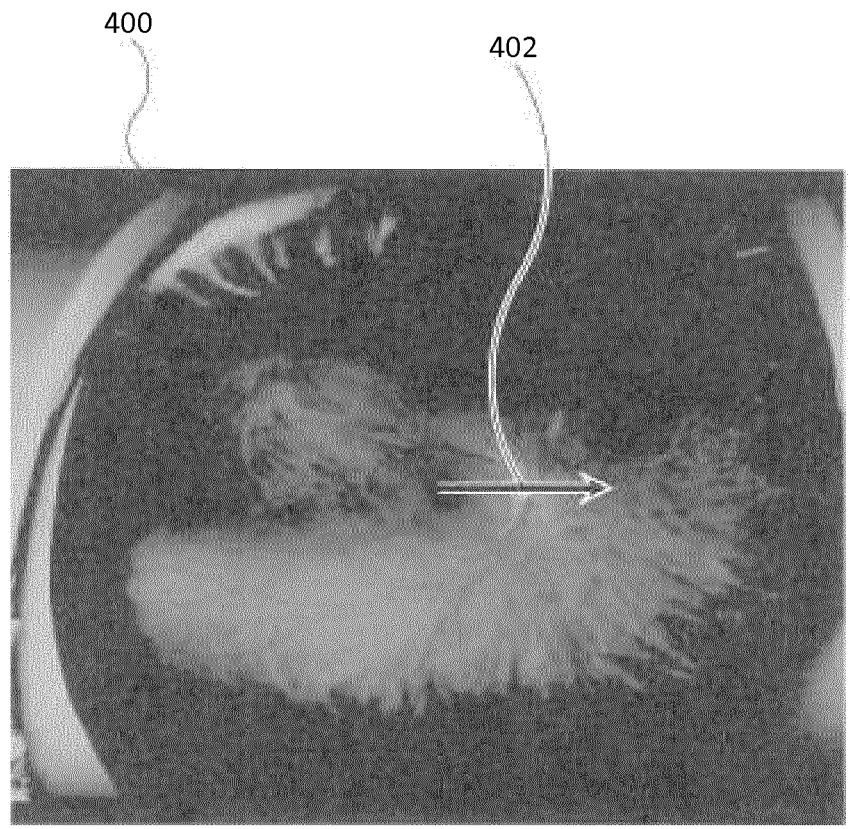
FIG. 5 is a diagram illustrating an example of an RG-SLO image.

At step 104, a desired capturing range of the OCT image is designated. The operator refers to the still image of the RG-SLO image displayed on the display 26, and operates the reception device 22 to designate the desired capturing range of the OCT image. For example, as illustrated in FIG. 5, an RG-SLO image 400 displayed on the display 26 is referred to, and a desired capturing range 402 is designated. The example of FIG. 5 illustrates a case in which the length of the desired capturing range in the Y direction is designated by the arrow. In this case, an OCT image of the region indicated by the desired capturing range 402 is captured.

Then, in a case in which designation of the desired capturing range has ended, the operator prompts the patient to look at the fixation target again. The patient thus looks at the fixation target again.

Figure 6:
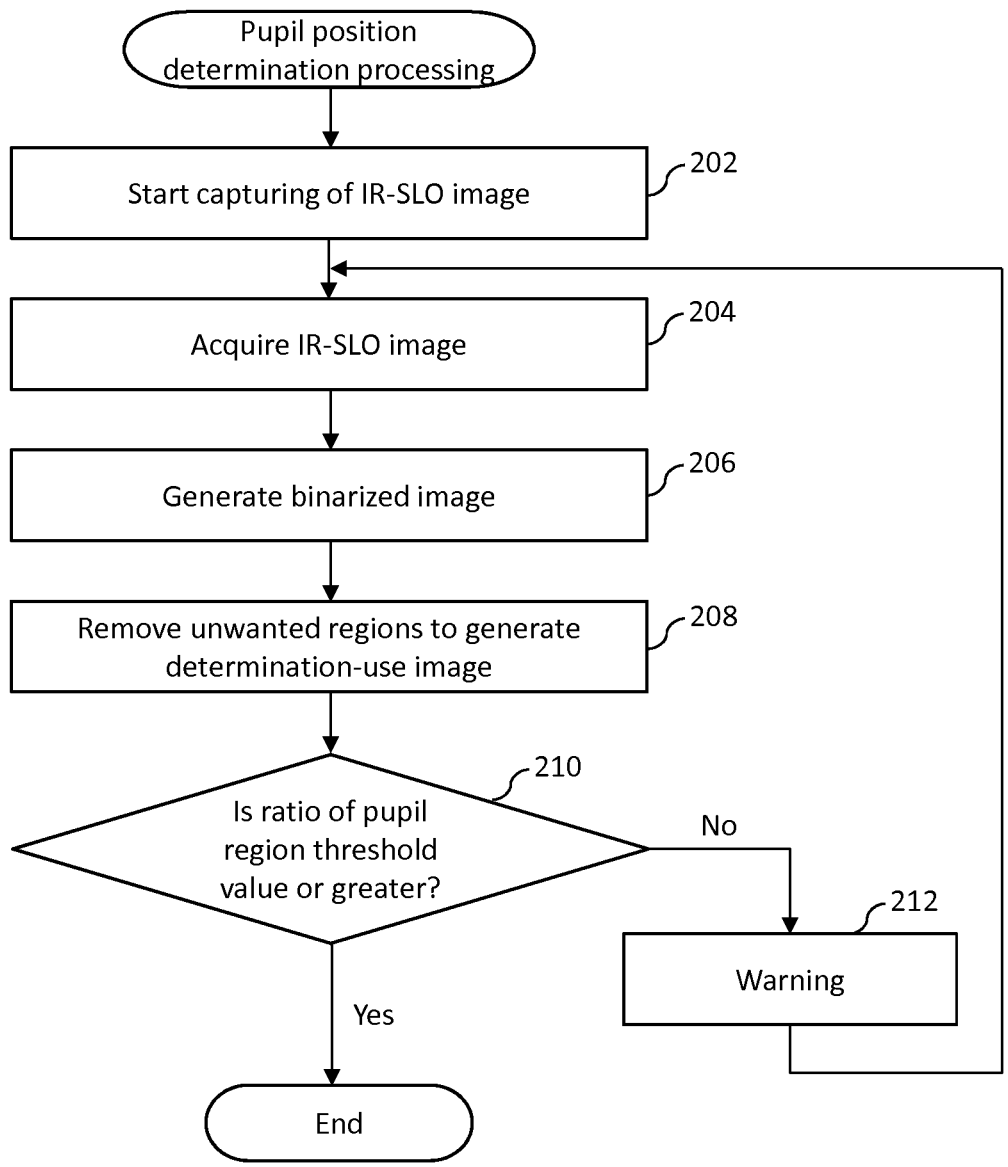
FIG. 6 is a flowchart illustrating an example of pupil position determination processing.

At step 105, the pupil position determination processing illustrated in FIG. 6 is executed. When an OCT image is captured over an ultra-wide angle region, namely, in a case in which the capturing target region of the OCT image is a peripheral portion of the subject's eye 38, the optical axis of light emitted from the SLD 50 for capturing the OCT image is liable to depart from the pupil of the subject's eye 38, and the quality of the OCT image is liable to deteriorate due to vignetting.

Thus, in the pupil position determination processing, determination is made by the determination module as to whether or not the position of the pupil of the subject's eye 38 is within a predetermined permissible range.

First, at step 202, capturing of an IR-SLO image by the ocular image capturing module is started. Namely, near-infrared light is emitted from the light source 40A, the SLO unit 32 is controlled such that the desired capturing range designated at step 104 of FIG. 4 is scanned, and a narrow-range IR-SLO image is captured. Note that capturing of IR-SLO images is executed successively until the processing of FIG. 4 ends. Moreover, although explanation is given regarding a case in which an IR-SLO image is captured in the present exemplary embodiment, an RG-SLO image (or other kind of image) may be captured.

At step 204, the narrow-range IR-SLO image generated by the SLO image generator 18 is acquired.

Figure 7:
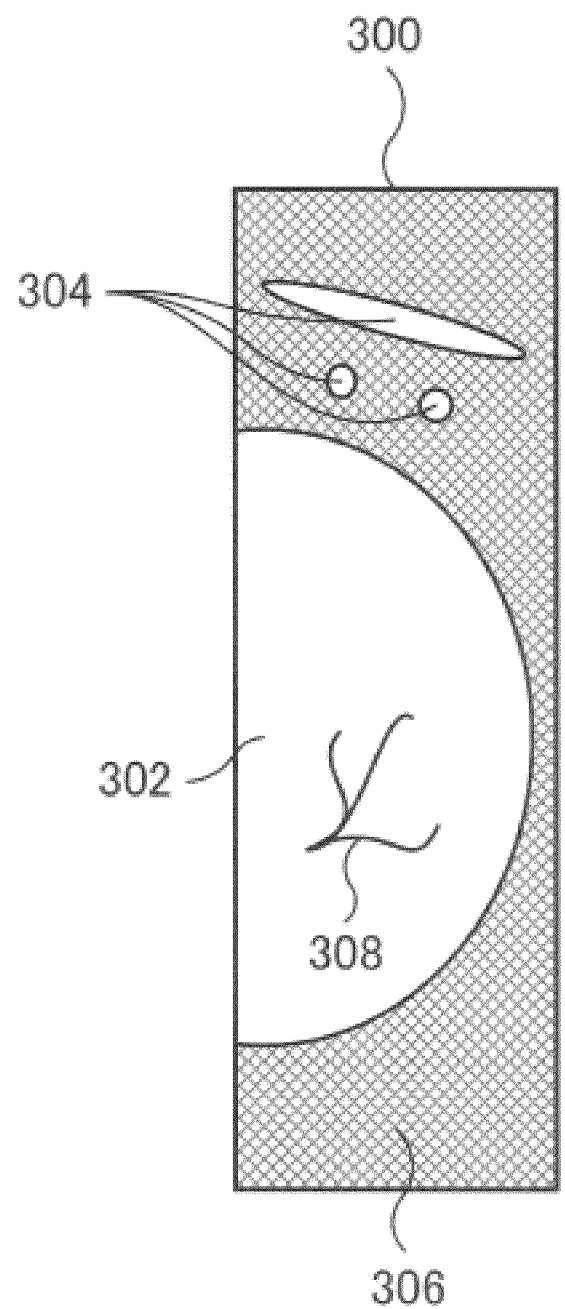
FIG. 7 is a diagram illustrating an example of a binarized image.

At step 206, binarization processing is optionally executed on the acquired IR-SLO image acquired by a binary image generation module that forms part of the ocular image generating module, and a binarized image is generated, this being the IR-SLO image binarized. Namely, for example, for each pixel of the IR-SLO image, a white pixel is given if the pixel value is a predetermined binarization threshold value or greater, or a black pixel is given if the pixel value is less than the binarization threshold value. FIG. 7 illustrates an example of a binarized image generated by the binary image generation module.

White regions in the binarized image 300 illustrated in FIG. 7 are regions onto which reflected light of light for IR-SLO imaging emitted toward the subject's eye 38 has been detected, and a white region 302 therein represents the pupil region of the subject's eye. Moreover, white regions 304 are regions other than the pupil, for example, an eyelash or eyelid region. Note that the white region 302 and the white regions 304 are sometimes connected. Moreover, a black region 306 is a region where the reflected light of the light for IR-SLO imaging emitted toward the subject's eye 38 has not been detected. As illustrated in FIG. 7, for example, a black region 308 such as a blood vessel sometimes appears in the white region 302 representing the pupil region.

Thus, sometimes white regions represent not only the pupil region, but also eyelash and eyelid regions. However, eyelash and eyelid white regions 304 are regions that are not needed in a case in which determining whether or not the position of the pupil is within the permissible range. Moreover, the black region 308 such as a blood vessel that has appeared in the white region 302 representing the pupil region is also a region not needed in a case in which determining whether or not the position of the pupil is in the permissible range.

Thus, at step 208, a determination-use image generating module, which may also form part of the ocular image generating module, optionally generates a determination-use image by removing unwanted regions other than the pupil from the binarized image 300 generated at step 206 (or from the captured image, in cases where binarization is not performed). In other words, the determination-use image generating module generates the determination-use image by removing from the binarized image 300 an unneeded region other than a binary image pupil region, the binary image pupil region being an image of at least a portion of the pupil in the binarized image 300. More specifically, for example, the white region 304 and the black region 308, which are unwanted regions, are removed from the binarized image 300 by executing known morphological operations on the binarized image 300.

Figure 8:
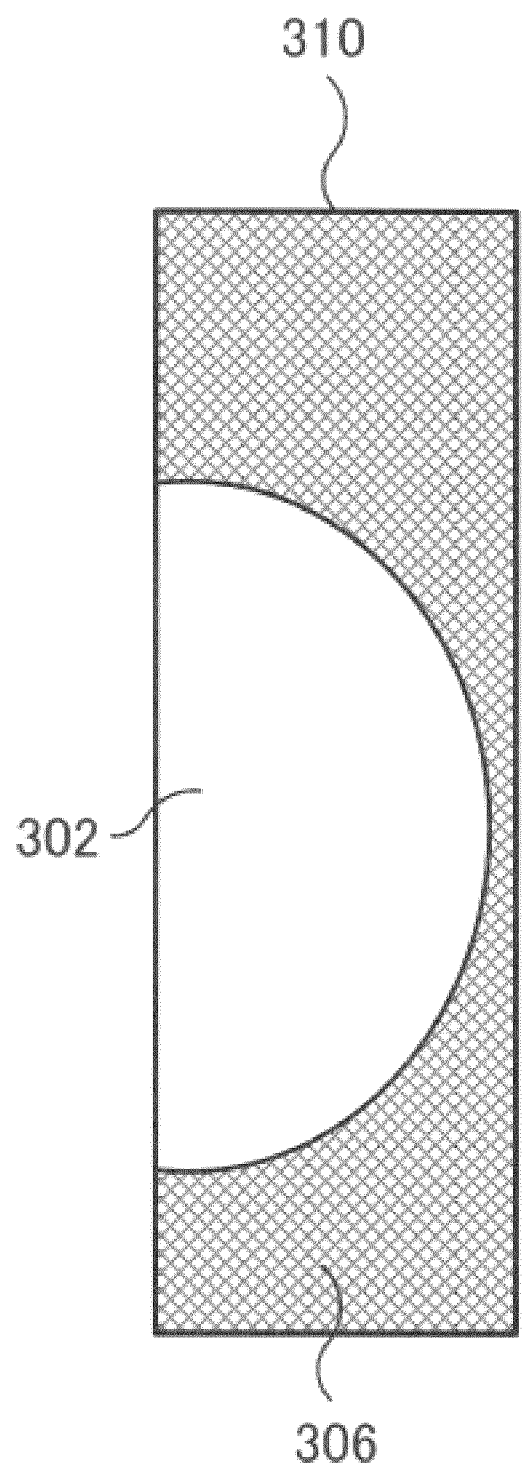
FIG. 8 is a diagram illustrating an example of a determination-use image.

Here, morphological operations is processing that leaves a feature portion of an image (the pupil in the present exemplary embodiment) and removes other unwanted regions by repeatedly performing downscale processing and upscale processing on a processing-target image. By executing such morphological operations on the binarized image 300, a determination-use image 310 from which the unwanted regions have been removed is generated, as illustrated in FIG. 8.

Note that although explanation has been given regarding a case in which unwanted regions are removed by morphological operations in the present exemplary embodiment, the processing that removes unwanted regions is not limited to morphological operations. For example, the unwanted regions may be removed using known feature extraction processing, pattern matching processing, or the like.

At step 210, the determination module determines whether or not at least a portion of a pupil region of the determination-use image 310 is within a predetermined permissible region within the determination-use image 310 (the pupil region being an image of at least a portion of the pupil of the subject's eye 38). Thus, a determination is made as to whether or not the position of the pupil is in the permissible range based on the determination-use image 310 generated at step 208.

Figure 9:
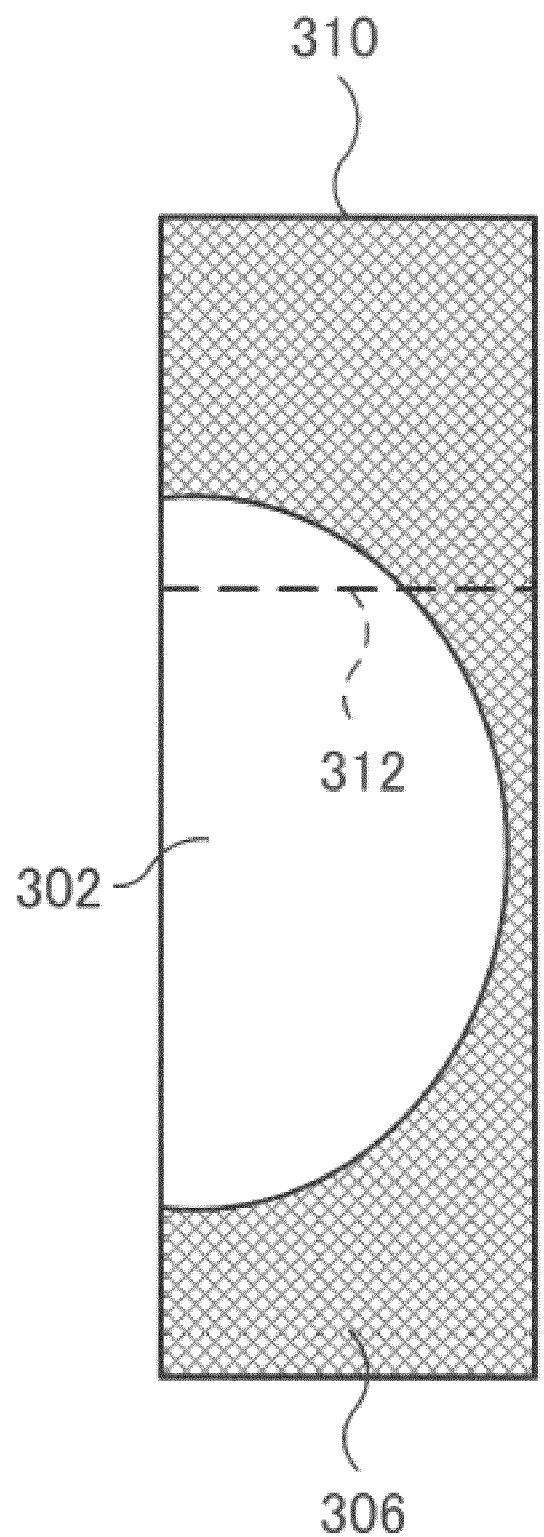
FIG. 9 is a diagram illustrating an example of a determination region in a determination-use image.

The determination module may alternatively determine whether or not a proportion of a predetermined permissible region of the determination-use image 310 that is occupied by at least a portion of a pupil region of the determination-use image 310 is a predetermined threshold value or greater. In other words, a determination may be made as to whether or not a ratio of a region occupied by the pupil in a predetermined determination region of the determination-use image 310 is a predetermined threshold value or greater. The determination region in the present exemplary embodiment is set to, for example, a line 312 running along a width direction (the X direction) of the determination-use image 310, as illustrated in FIG. 9. Then, determination is made as to whether or not the ratio of the number of pixels occupied by white pixels (pixels representing the pupil) on the line 312 to the total number of pixels on the line 312 is the threshold value or greater. Here, the threshold value is set to a value such that the quality of the subsequently imaged OCT image will be in a permissible range when the number of white pixels is the threshold value or greater.

Then, the present routine ends in a case in which the ratio of the number of pixels occupied by white pixels on the line 312 to the total number of pixels on the line 312 is the threshold value or greater, or processing transitions to step 212 in a case in which the ratio is less than the threshold value.

At step 212, the determination module generates an output signal that is indicative of the determination. The primary controller 14 may control the display controller 24, on the basis of the output signal generated by the determination module, to set the display content that is displayed on the display 26, for example a warning message stating that the OCT image will not be imaged normally. The operator then instructs the patient to look at the fixation target. Then, the above processing is repeated until the determination of step 210 is an affirmative determination.

Figure 10:
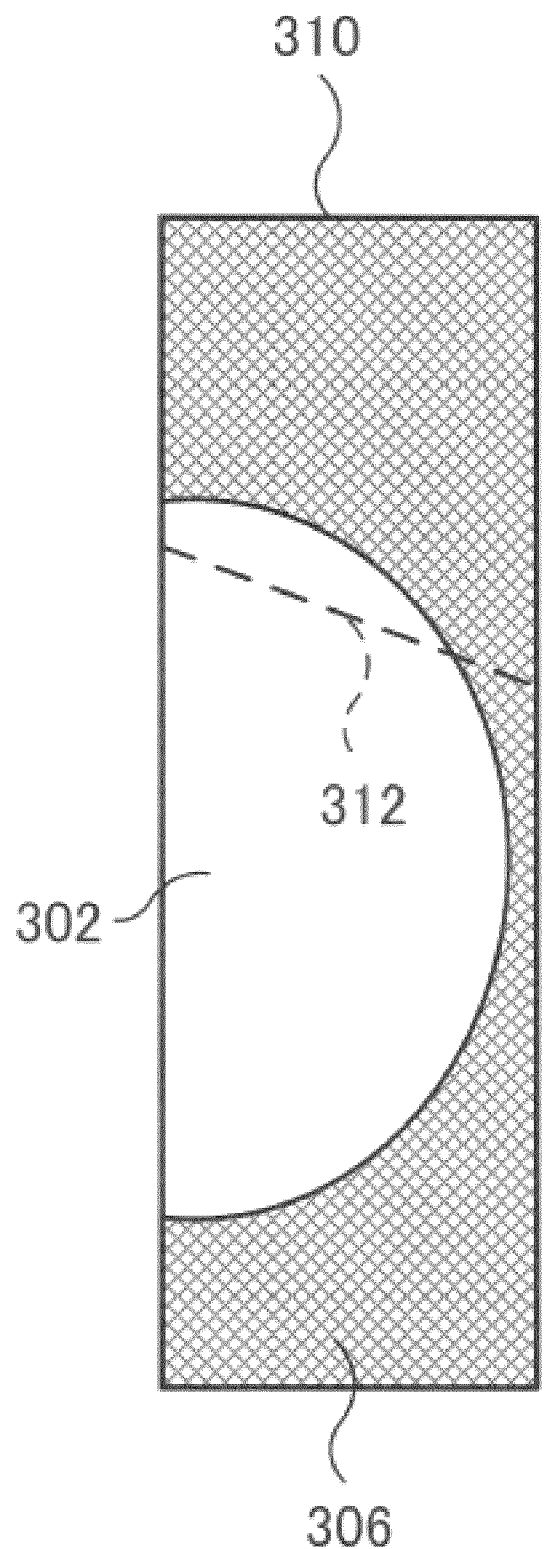
FIG. 10 is a diagram illustrating an example of a determination region in a determination-use image.
Figure 11:
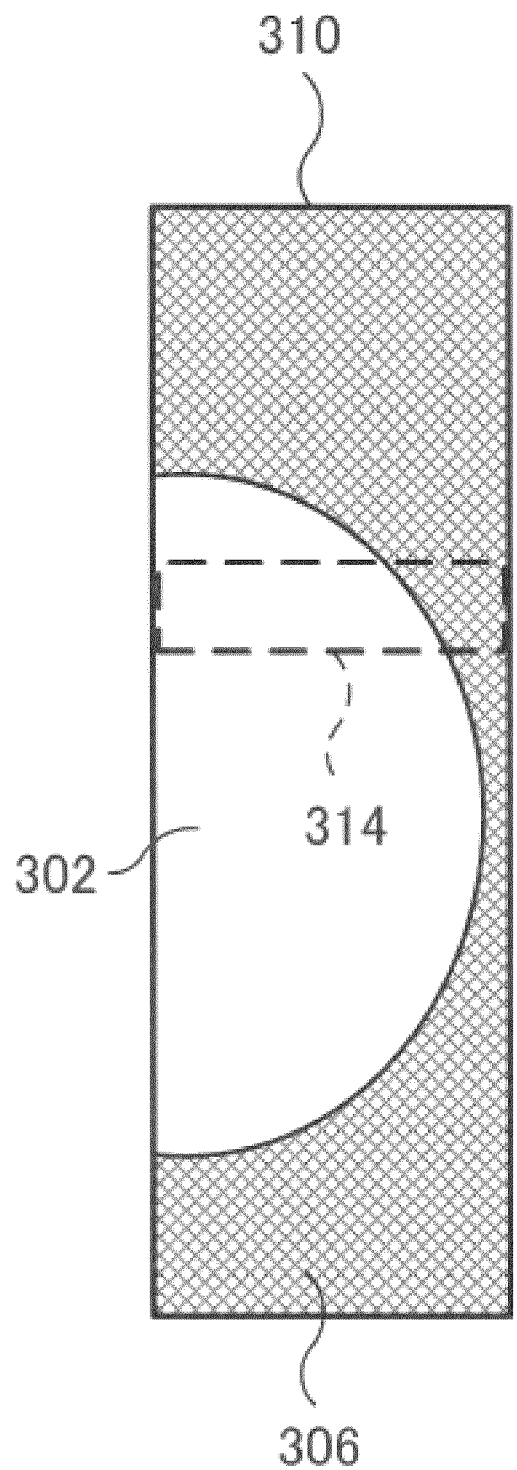
FIG. 11 is a diagram illustrating an example of a determination region in a determination-use image.

Note that although the line 312 is a line along the width direction of the determination-use image 310 in FIG. 9, the line 312 may be inclined with respect to the width direction of the determination-use image 310 as illustrated in FIG. 10. Moreover, the determination region may be a rectangular region 314 as illustrated in FIG. 11. Moreover, the determination region may be a freely selected polygonal region other than that of a rectangle.

Returning to FIG. 4, at step 106, automatic alignment processing is executed to match a capturing range of the OCT image to the desired capturing range designated at step 104.

More specifically, a narrow-range IR-SLO image generated by the SLO image generator 18 is acquired, and a positional offset between the narrow-range IR-SLO image and the desired capturing range designated at step 104 is calculated based on the acquired narrow-range IR-SLO image and the wide-range RG-SLO image imaged at step 102. Then, a scanning range in the capturing of the OCT image is set based on the calculated positional offset.

At step 108, auto-focus processing and auto-reference processing are executed in the capturing of the OCT image.

First, capturing of the OCT image is started. Namely, low coherence light is emitted from the SLD 50, the OCT unit 34 is controlled so as to scan in the scanning range set at step 106, and the OCT image is captured. Note that capturing of the OCT image is executed successively until the present routine ends.

Then, the OCT unit 34 is controlled so that the captured OCT image is focused, namely, so as to correct for a positional offset in a Z direction (auto-focus processing).

Moreover, the OCT unit 34 is controlled such that the depth direction (Z direction) of the captured OCT image is placed within a predetermined range (auto-reference processing).

At step 110, the captured OCT image is stored in the secondary storage section 78 and displayed on the display 26.

Note that the eyeball may also move slightly due to involuntary eye movements even in a case in which the patient is looking at the fixation target.

Eye tracking processing is therefore executed in parallel with the processing of step 110 in order to correct positional offset caused by involuntary eye movement.

In eye tracking processing, for example, an IR-SLO image taken immediately after starting capturing of the OCT image at step 108, from out of successively captured IR-SLO images, is set as a reference-use IR-SLO image. Then, subsequently imaged IR-SLO images are set as tracking-use IR-SLO images, positional displacement from the reference-use IR-SLO image is calculated, and the OCT unit 34 is controlled so as to correct the calculated positional offset. This processing is executed each time a tracking-use IR-SLO image is acquired.

Thus, at step 110, the OCT image is captured by following eyeball movements caused by involuntary eye movement.

Figure 12:
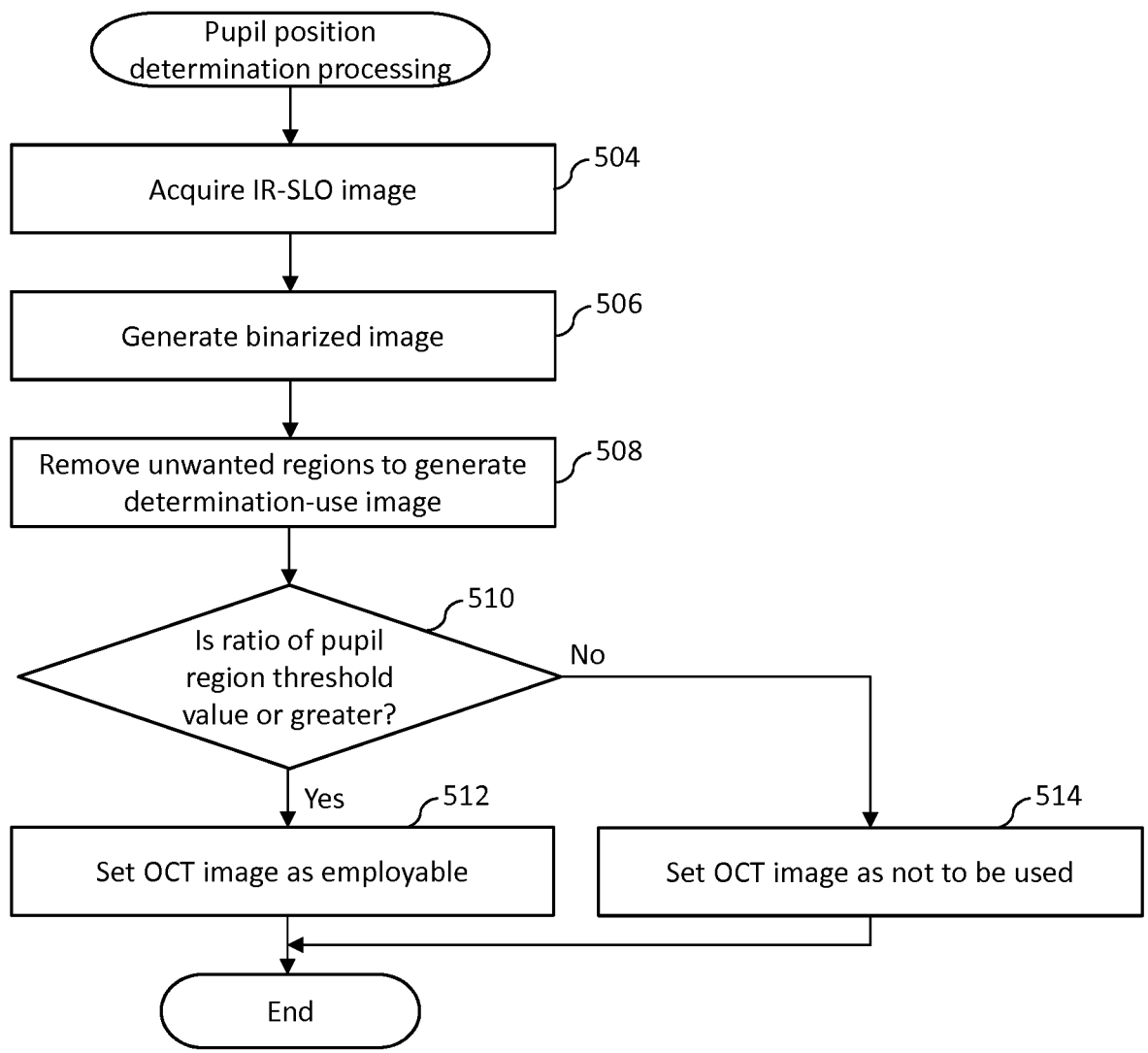
FIG. 12 is a flowchart illustrating an example of pupil position determination processing.

Moreover, the pupil position determination processing illustrated in FIG. 12 is executed in parallel with the processing of step 110 and the eye tracking processing.

At steps 504 to 510 illustrated in FIG. 12, processing similar to that of steps 204 to 210 illustrated in FIG. 6 is executed, and explanation thereof is omitted.

At step 512, the secondary storage section 78 is stored with information that sets, as being employable as determination information indicating the determination result of step 208, an OCT image captured at step 110 at a timing matching the timing at which the IR-SLO image was acquired at step 504.

At step 514, the secondary storage section 78 is stored with information that sets an OCT image imaged at step 110 at a timing matching the timing at which the IR-SLO image was acquired at step 504, as not to be used as determination information indicating the determination result of step 208.

At step 110 of FIG. 4, the determination information stored in the secondary storage section 78 is referenced by the pupil position determination processing of FIG. 12, the OCT image set as not to be used is erased from the secondary storage section 78, and the OCT image is set as not to be used.

Then, in a case in which a timing at which capturing of the OCT image is to end has been reached, capturing of the IR-SLO image and capturing of the OCT image are stopped and the present routine ends.

Thus, in the present exemplary embodiment, determination as to whether or not the position of the pupil is in the permissible range is made using not only the anterior segment of the subject's eye, but also the IR-SLO image based on reflected light from the posterior segment, enabling alignment of the pupil to be performed more precisely. Moreover, since the OCT image is set as not to be used in a case in which the position of the pupil is outer side of the permissible range, OCT images having poor precision are prevented from being used to generate tomographic images.

Figure 13:
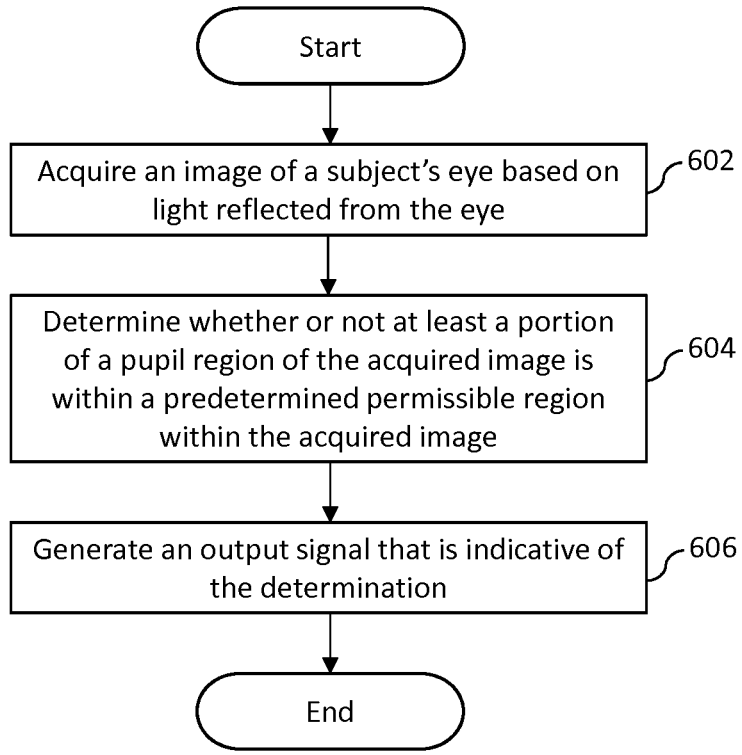
FIG. 13 is a flow chart summarizing an ocular image processing method performed by the determination module.

The ocular image processing method performed by the determination module is summarised in the flow chart of FIG. 13. In process 602, the determination module acquires an image of a subject's eye 38 based on light reflected from the eye 38. In process S604, the determination module determines whether or not at least a portion of a pupil region of the acquired image is within a predetermined permissible region within the acquired image, the pupil region being an image of at least a portion of the pupil of the eye 38. In process S606, the determination module generates an output signal that is indicative of the determination.

Figure 14:
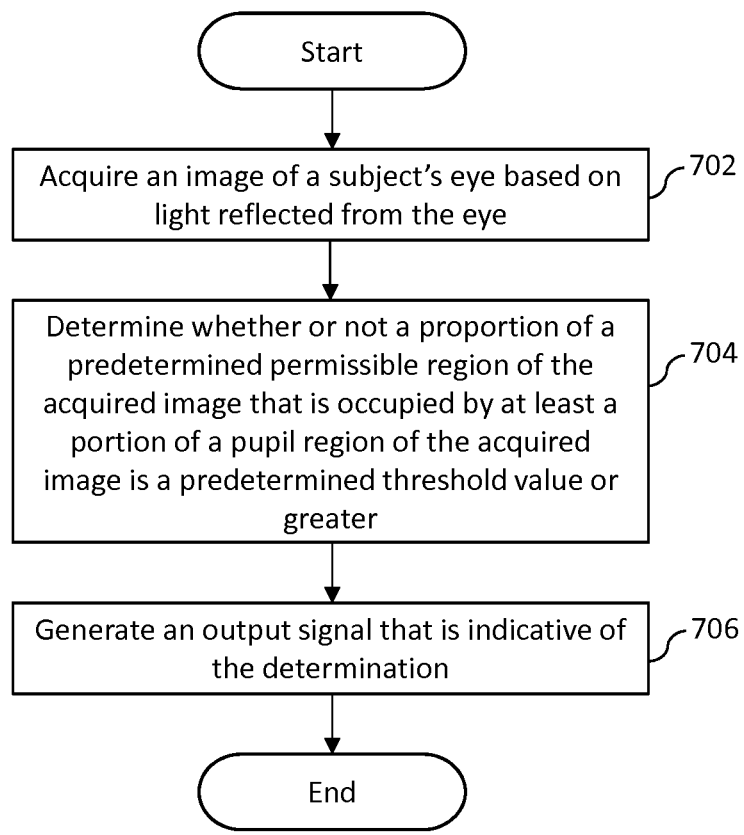
FIG. 14 is a flow chart summarizing an alternative ocular image processing method performed by the determination module.

An alternative ocular image processing method performed by the determination module is summarised in the flow chart of FIG. 14. In process 702, the determination module acquires an image of a subject's eye 38 based on light reflected from the eye. In process S704, the determination module determines whether or not a proportion of a predetermined permissible region of the acquired image that is occupied by at least a portion of a pupil region of the acquired image is a predetermined threshold value or greater, the pupil region being an image of at least a portion of the pupil of the eye 38. In process 706, the determination module generates an output signal that is indicative of the determination.

In a variant of the above-described embodiment, the primary controller 14 may function as a fixation target display controller to control at least one characteristic of the displayed fixation target (e.g. a colour of at least a portion of the fixation target, a flashing of at least a portion of the fixation target, etc.) based on an output signal from the determination module that is indicative of the determination made, in order to provide the subject with feedback on the degree of pupil alignment and thus assist the subject in maintaining appropriate pupil alignment.

Explanation has been given in the present exemplary embodiment regarding a case in which the binarization threshold value is set to 1 when generating the binarized image from the IR-SLO image in the pupil position determination processing; however, the IR-SLO image may, for example, be divided into plural regions according to brightness levels, and an appropriate binarization threshold value may be set for each of the plural regions.

An imaging device such as a CCD or a CMOS may be additionally provided, and the image imaged by the imaging device may replace the RG-SLO image. Moreover, the imaging device may be provided instead of the SLO unit 32, and images imaged by the imaging device may replace the RG-SLO image and the IR-SLO image.

Moreover, the pupil position determination processing may be applied to the RG-SLO image imaged at step 102. Namely, after capturing the RG-SLO image at step 102, the processing of steps 204 to 212 of the pupil position determination processing illustrated in FIG. 6 may be executed on the imaged RG-SLO image. RG-SLO images in which the position of the pupil is outer side of the permissible range can thereby be prevented from being employed at step 104.

Although examples have been given in each of the exemplary embodiments above in which a pair of concave mirrors are formed by the slit mirror 66 and the ellipsoid mirror 70, the present invention is not limited thereto. For example, a tilted spherical mirror, a non-spherical mirror, a pair of parabola mirrors, a pair of parabolic mirrors, a lens system, or an optical system employing an appropriate combination of these may be employed instead of the slit mirror 66.

In the exemplary embodiments explained above, explanation has been given regarding examples in which the polygon mirror 44 that scans in the Y direction and the V-galvanometer mirror 60 that scans in the Y direction are disposed at the light incidence side of the dichroic mirror 64. However, the dichroic mirror 64 may be disposed in a position separated in the optical axis direction from the focal point of a slit mirror, and the polygon mirror 44 or the V-galvanometer mirror 60 that scans in the Y direction may be disposed at the focal point position of the slit mirror. In such cases, the polygon mirror 44 or the V-galvanometer mirror 60 functions as a shared scanning optical system employed during SLO image acquisition and OCT image acquisition.

Moreover, although explanation has been given regarding an example in which a shared optical axis through which light for SLO and light for OCT passes is generated by the dichroic mirror 64, a beam splitter such as a polarizing beam splitter or an optical member such as a half mirror may be employed instead of the dichroic mirror 64.

Figure 15A:
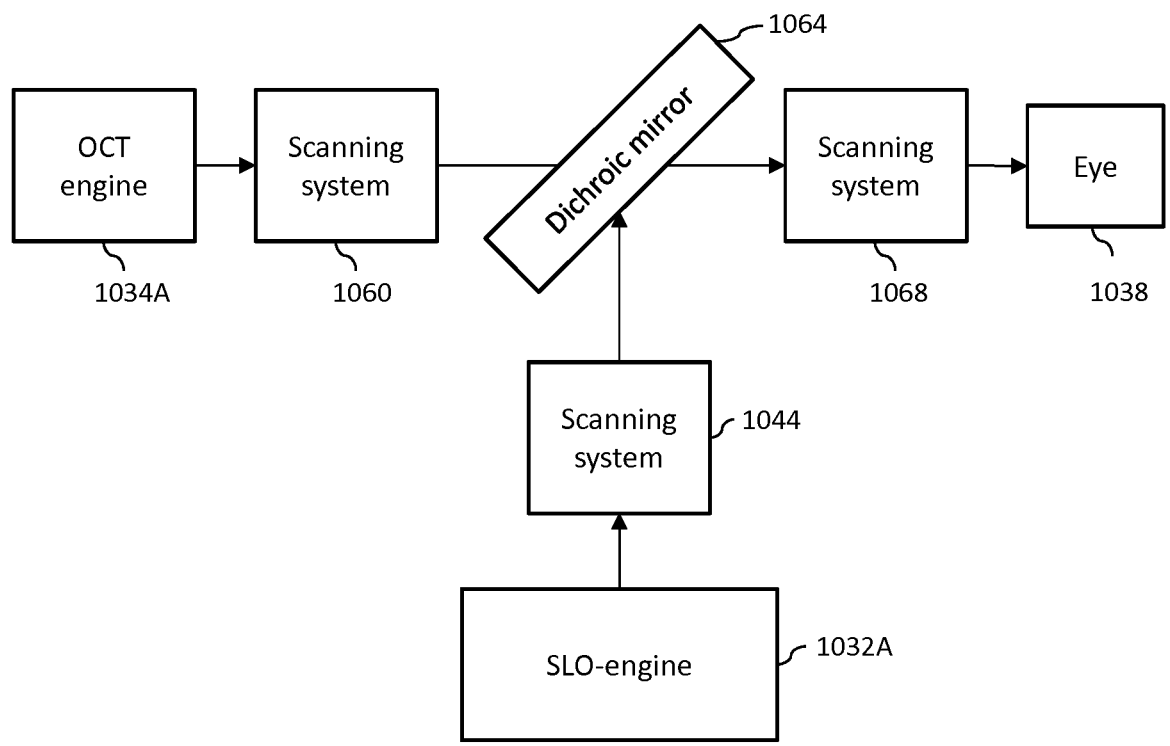
FIG. 15 (A) is a diagram corresponding to the scanning optical system of FIG. 1.
Figure 15B:
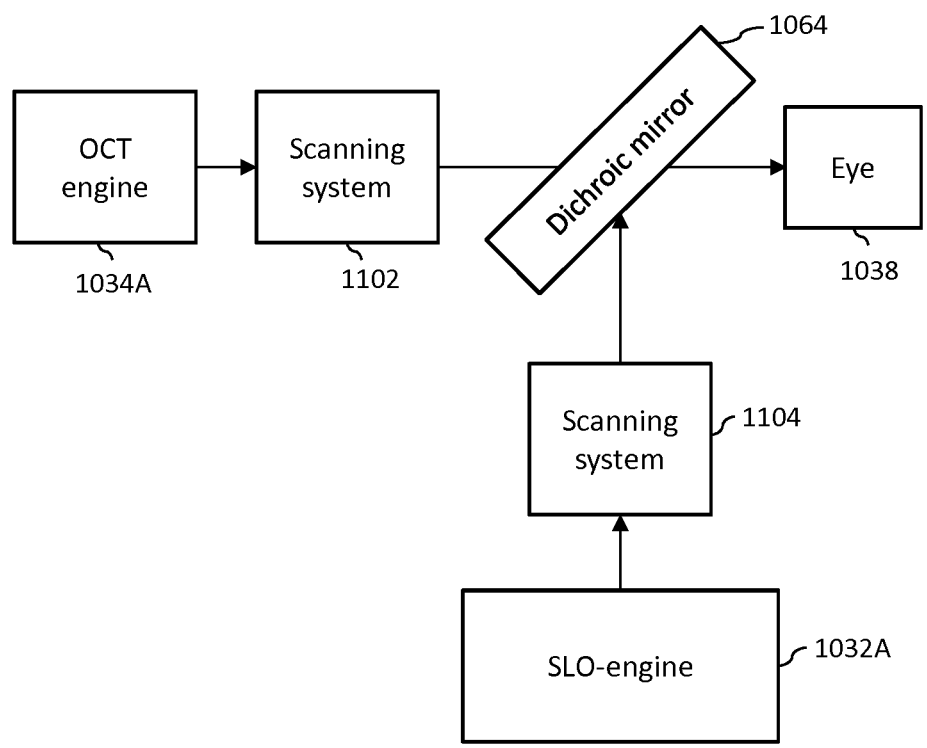
Figure 15C:
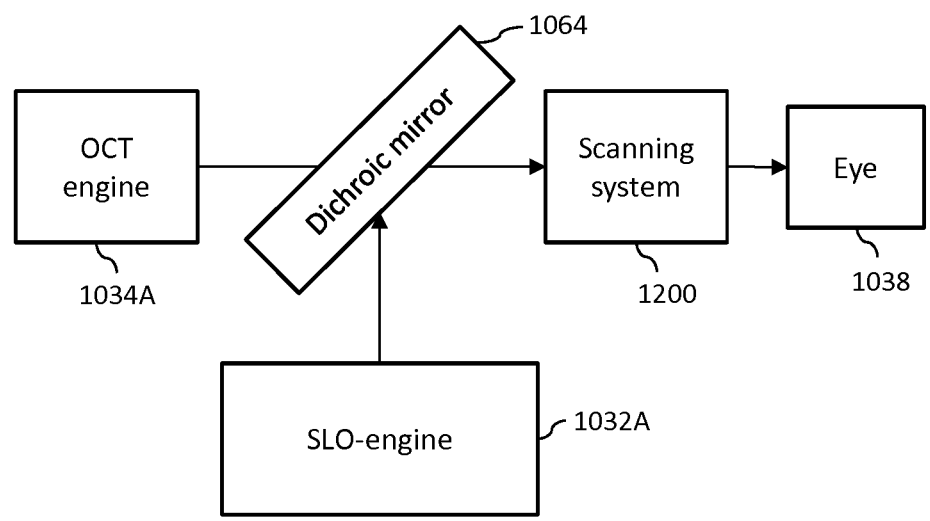

Explanation has been given in each of the exemplary embodiments explained above regarding examples in which, as illustrated in FIG. 1, the polygon mirror 44 and the V-galvanometer mirror 60 are disposed at the light incidence side of the dichroic mirror 64, and the H-galvanometer mirror 68 for X direction scanning, shared by SLO and OCT, is disposed at the light emission side of the dichroic mirror 64. FIG. 15 (A) illustrates a configuration corresponding to the SLO unit 32, the OCT unit 34, and the shared optical system 36 illustrated in FIG. 1. As illustrated in FIG. 15 (A), a device main body includes a dichroic mirror 1064, an SLO engine 1032A, and an OCT engine 1034A. A scanning system 1044 is disposed between the dichroic mirror 1064 and the SLO engine 1032A. Moreover, a scanning system 1060 is disposed between the dichroic mirror 1064 and the OCT engine 1034A. A scanning system 1068 is disposed between the dichroic mirror 1064 and a subject's eye 1038.

Note that the scanning system 1044 corresponds to the polygon mirror 44, and the SLO engine 1032A is a portion obtained by removing the polygon mirror 44 from the SLO unit 32 in FIG. 1. The scanning system 1060 corresponds to the V-galvanometer mirror 60, and the OCT engine 1034A is a portion obtained by removing the V-galvanometer mirror 60 from the OCT unit 34 in FIG. 1. The scanning system 1068 corresponds to the H-galvanometer mirror 68.

The following modifications can be can be made to the scanning optical system.

FIG. 15 (B) illustrates a first modified example of a scanning optical system. As illustrated in FIG. 15 (B), a two-dimensional scanning optical system 1104 for SLO is disposed on one light incidence side (the SLO engine 1032A side) of the dichroic mirror 1064, and a two-dimensional scanning optical system 1102 for OCT is disposed at another light incidence side (the OCT engine 1034A side) of the dichroic mirror 1064.

FIG. 15 (C) illustrates a second modified example of a scanning optical system. As illustrated in FIG. 15 (C), a shared two-dimensional scanning optical system 1200, employed by SLO and OCT, is disposed at the light emission side of the dichroic mirror 1064.

Moreover, it also goes without saying that in the all of the scanning optical systems explained above, similar scanning can be performed by exchanging the X direction with the Y direction.

Although explanation has been given regarding examples in which an ellipsoid mirror is employed as an optical member that relays the scanning, another concave mirror such as a parabolic mirror may be employed, or an optical member such as a lens may be employed instead of a concave mirror. An optical member that includes plural focal points may be employed as the optical member that relays the scanning. In such cases, the positional relationship between the optical member, the scanning optical system, and the subject's eye may adopt the following aspects.

In a first aspect, the subject's eye is disposed at one focal point position f1, and a shared two-dimensional scanning optical system, employed by SLO and OCT, is disposed at another one focal point position f2.

In a second aspect, the subject's eye is disposed at one focal point position f1, a two-dimensional scanning optical system employed by SLO is disposed at another one focal point position f2, and a two-dimensional scanning optical system employed by OCT is disposed at yet another one focal point position f3.

In a third aspect, the subject's eye is disposed at one focal point position f1, a shared one-dimensional scanning optical system employed by both SLO and OCT and that scans light in a first direction is disposed at another one focal point position f2, a one-dimensional scanning optical system that scans light in a second direction intersecting the first direction (for example, an orthogonal direction) employed by SLO is disposed at yet another one focal point position f3, and a one-dimensional scanning optical system that scans light in a second direction employed in OCT is disposed at an optically equivalent position to the another one focal point position f3.

Note that in each of the aspects above, the subject's eye and a scanning optical system may be disposed at a position optically equivalent to a focal point position instead of a focal point position.

Although examples have been given in each of the exemplary embodiments above in which a pair of concave mirrors are formed by the slit mirror 66 and the ellipsoid mirror 70, the present invention is not limited thereto. For example, a tilted spherical mirror, a non-spherical mirror, a pair of paraboloidal mirrors, a pair of parabolic mirrors, a lens system, or an optical system employing an appropriate combination of these may be employed instead of the slit mirror 66.

Figure 16:
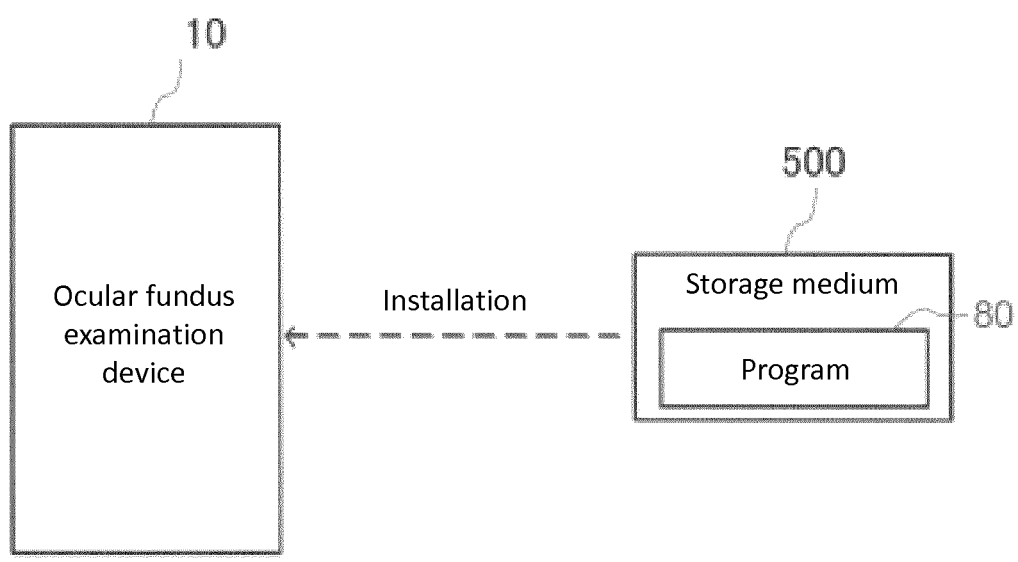
FIG. 16 is a conceptual diagram illustrating an example of an aspect of installing an ocular image capturing program in an ocular image capturing device from a storage medium stored with the ocular image capturing program.

Although examples have been given of cases in which the ocular fundus image capturing program 80 of each of the exemplary embodiments above are read from the secondary storage section 78, the ocular fundus image capturing program 80 does not necessarily need to be stored on the secondary storage section 78 from the outset. For example, as illustrated in FIG. 16, the ocular fundus image capturing program 80 may first be stored on a freely selected portable storage medium 90, such as a solid state drive (SSD), universal serial bus (USB) memory, or a compact disc read only memory (CD-ROM). In such cases, the ocular image capturing program 80 of the storage medium 90 is installed in the ocular image capturing device 10, and the installed ocular fundus image capturing program 80 is executed by the CPU 74.

The ocular image capturing program 80 may be stored in a storage section of another computer, server device, or the like connected to the ocular image capturing device 10 through a communication network (not illustrated in the drawings), and the ocular image capturing program 80 may be downloaded in accordance with a request by the ocular image capturing device 10. In such cases, the downloaded ocular fundus image capturing program 80 is executed by the CPU 74.

Moreover, the ocular fundus image capturing processing explained in each of the exemplary embodiments above are merely examples. It therefore goes without saying that unnecessary steps may be omitted, new steps may be added, and the processing sequence may be rearranged within a range not departing from the spirit of the present invention. Moreover, each item of processing included in the ocular fundus image capturing processing may be implemented by hardware configuration alone, such as an FPGA, an ASIC, or the like, or may be implemented by a combination of a computer employing software configuration and hardware configuration.

In addition, the configuration of the ocular image capturing device 10 (see FIG. 1) explained in each of the exemplary embodiments above is merely an example. It goes without saying that unnecessary portions may be removed and new portions may be added within a range not departing from the spirit of the present invention.

Moreover, the flow of processing of the ocular fundus image capturing program explained in each of the exemplary embodiments above are merely examples (see FIG. 4 and FIG. 6). It goes without saying that unnecessary steps may be omitted, new steps may be added, and the processing sequence may be rearranged within a range not departing from the spirit of the present invention.

All publications, patent applications and technical standards mentioned in the present specification are incorporated by reference in the present specification to the same extent as if each individual publication, patent application, or technical standard was specifically and individually indicated to be incorporated by reference.

EXPLANATION OF THE REFERENCE NUMERALS

10 ocular image capturing device
13 controller
14 primary controller
16 OCT image generator
18 SLO image generator
32 SLO unit
34 OCT unit
36 shared optical system
38 subject's eye

The invention claimed is:

1. An ocular image capturing device comprising:
an ocular image generating module operable to generate an image of a subject's eye based on light reflected from the eye; and
a determination module arranged to perform a comparison to determine whether or not a proportion of a predetermined permissible region of the generated image that is indicative of at least a portion of a pupil region of the generated image is equal to or greater than a predetermined threshold value, and to generate an output signal that is indicative of a determination by the determination module, the pupil region being an image of at least a portion of a pupil of the eye.

2. An ocular image processing method comprising:
acquiring an image of a subject's eye based on light reflected from the eye;
determining whether or not at least a portion of a pupil region of the acquired image is within a predetermined permissible region within the acquired image, the pupil region being an image of at leas a portion of a pupil of the eye, wherein the predetermined permissible region is fixed in shape; and
generating an output signal that is indicative of a result of the determining.

3. An ocular image processing method comprising:
acquiring an image of a subject's eye based on light reflected from the eye;
performing a comparison to determine whether or not a proportion of a predetermined permissible region of the acquired image that is indicative of at least a portion of a pupil region of the acquired image is equal to or greater than a predetermined threshold value, the pupil region being an image of at least a portion of a pupil of the eye; and
generating an output signal that is indicative of a result of the determining.

4. A non-transitory storage medium storing computer program instructions which, when executed by a processor, cause the processor to perform the method of claim 2.

5. An ocular image capturing device comprising:
an ocular image generating module operable to generate an image of a subject's eye based on light reflected from the eye; and
a determination module arranged to perform a determination to determine whether or not at least a portion of a pupil region of the generated image is within a predetermined permissible region within the generated image, and to generate an output signal that is indicative of a determination by the determination module, the pupil region being an image of at least a portion of a pupil of the eye, wherein the predetermined permissible region is fixed in shape.

6. The ocular image capturing device of claim 5, wherein the ocular image generating module comprises:
- an ocular image capturing module arranged to capture an image of the subject's eye based on light reflected from the eye; and
- a determination-use image generating module arranged to generate a determination-use image by removing from the captured image an unneeded region other than a captured image pupil region, the captured image pupil region being an image of at least a portion of the pupil in the captured image,
- wherein the determination module is arranged to perform the determination based on the determination-use image.

7. The ocular image capturing device of claim 5, wherein the ocular image generating module comprises:
- an ocular image capturing module arranged to capture an image of the subject's eye based on light reflected from the eye;
- a binary image generation module arranged to generate a binary image by binarizing the captured image; and
- a determination-use image generating module arranged to generate a determination-use image by removing from the binary image an unneeded region other than a binary image pupil region, the binary image pupil region being an image of at least a portion of the pupil in the binary image,
- wherein the determination module is arranged to perform the determination based on the determination-use image.

8. The ocular image capturing device of claim 5, further comprising an illumination module arranged to illuminate an ocular fundus of the subject's eye, wherein
- the ocular image generating module comprises an ocular image capturing module arranged to capture an image of the subject's eye based on light reflected from the eye, and
- a field-of-view of the illumination module has a predetermined relationship to a field-of-view of the ocular image capturing module.

9. The ocular image capturing device of claim 8, further comprising a controller arranged to control the illumination module based on the output signal generated by the determination module.

10. The ocular image capturing device of claim 8, wherein the determination module is arranged to repeatedly perform the determination while the illumination module is illuminating the ocular fundus, the ocular image capturing device further comprising a storage module arranged to store results of determinations performed by the determination module.

11. The ocular image capturing device of claim 8, wherein the illumination module comprises a tomographic image acquisition module arranged to acquire a tomographic image of the ocular fundus of the subject's eye using interference, from light that has been emitted toward the subject's eye, between reflected light from the ocular fundus of the subject's eye and reference light that has passed along an optical pathway different from an optical pathway of the reflected light.

12. The ocular image capturing device of claim 5, further comprising:
- a tomographic image acquisition module arranged to acquire a tomographic image of the ocular fundus of the subject's eye using interference, from light that has been emitted toward the subject's eye, between reflected light from an ocular fundus of the subject's eye and reference light that has passed along an optical pathway different from an optical pathway of the reflected light; and
- a control module arranged to control acquisition of the tomographic image by the tomographic image acquisition module based on the determination performed by the determination module.

13. The ocular image capturing device of claim 12, wherein the ocular image generating module comprises:
- a first light source arranged to emit light for imaging the ocular fundus;
- a first scanning optical system arranged to scan light in a first direction and that scans light in an ultra-wide field in a second direction intersecting the first direction; and
- a first optical receiver arranged to receive light from the ocular fundus of the subject's eye in a case in which the subject's eye has been scanned by the first scanning optical system using light emitted from the first light source, wherein the tomographic image acquisition module includes:
- a second light source arranged to emit light for generating a tomographic image;
- a second scanning optical system arranged to scan light in the first direction and that scans light in an ultra-wide field in the second direction;
- a second optical receiver arranged to receive, from light emitted from the second light source by the second scanning optical system, reflected light from the ocular fundus of the subject's eye and reference light that has passed along an optical pathway different from an optical pathway of the reflected light; and
- a generating module arranged to generate the tomographic image based on the reflected light and the reference light received by the second optical receiver.

14. The ocular image capturing device of claim 5, further comprising:
- a fixation target display module arranged to display a fixation target for fixing a gaze of the subject's eye; and
- a fixation target display controller arranged to control at least one characteristic of the displayed fixation target based on the output signal generated by the determination module.

15. The ocular image capturing device of claim 5, further comprising:
- a display; and
- a display controller arranged to set a display content of the display based on the output signal generated by the determination module.

* * * * *